US010252977B2

(12) United States Patent
Hillebrand et al.

(10) Patent No.: US 10,252,977 B2
(45) Date of Patent: Apr. 9, 2019

(54) HALOGEN-SUBSTITUTED PHENOXYPHENYLAMIDINES AND THE USE THEREOF AS FUNGICIDES

(71) Applicant: Bayer Cropscience Aktiengesellschaft, Monheim am Rhein (DE)

(72) Inventors: Stefan Hillebrand, Neuss (DE); Mazen Es-Sayed, Langenfeld (DE); Joerg Greul, Leverkusen (DE); Ulrike Wachendorff-Neumann, Neuwied (DE); Juergen Benting, Leichlingen (DE); Stephane Brunet, St Andre de Corcy (FR)

(73) Assignee: BAYER CROPSCIENCE AKTIENGESELLSCHAFT, Monheim am Rhein (DE)

( * ) Notice: Subject to any disclaimer, the term of this patent is extended or adjusted under 35 U.S.C. 154(b) by 0 days.

(21) Appl. No.: 15/736,242

(22) PCT Filed: Jun. 10, 2016

(86) PCT No.: PCT/EP2016/063254
§ 371 (c)(1),
(2) Date: Dec. 13, 2017

(87) PCT Pub. No.: WO2016/202688
PCT Pub. Date: Dec. 22, 2016

(65) Prior Publication Data
US 2018/0186724 A1 Jul. 5, 2018

(30) Foreign Application Priority Data
Jun. 15, 2015 (EP) .................................... 15172106

(51) Int. Cl.
C07C 205/38 (2006.01)
C07C 257/12 (2006.01)
C07C 217/90 (2006.01)
A01N 37/52 (2006.01)

(52) U.S. Cl.
CPC ............ *C07C 205/38* (2013.01); *A01N 37/52* (2013.01); *C07C 217/90* (2013.01); *C07C 257/12* (2013.01)

(58) Field of Classification Search
None
See application file for complete search history.

(56) References Cited

U.S. PATENT DOCUMENTS

| 2006/0052459 | A1 | 3/2006 | Vors et al. |
| 2007/0155802 | A1 | 7/2007 | Labourdette et al. |
| 2008/0255196 | A1 | 10/2008 | Kunz et al. |
| 2008/0255208 | A1 | 10/2008 | Luemmen et al. |
| 2008/0280992 | A1 | 11/2008 | Kunz et al. |
| 2009/0018176 | A1 | 1/2009 | Dahmen et al. |
| 2009/0042994 | A1 | 2/2009 | Luemmen et al. |
| 2009/0082351 | A1 | 3/2009 | Kunz et al. |
| 2009/0143431 | A1 | 6/2009 | Kunz et al. |
| 2009/0197918 | A1 | 8/2009 | Kunz et al. |
| 2010/0093534 | A1 | 4/2010 | Kunz et al. |
| 2010/0099558 | A1 | 4/2010 | Kunz et al. |
| 2010/0105552 | A1 | 4/2010 | Kunz et al. |
| 2010/0105553 | A1 | 4/2010 | Kunz et al. |
| 2010/0113276 | A1 | 5/2010 | Kuhn et al. |
| 2011/0130282 | A1 | 6/2011 | Kunz et al. |
| 2011/0143937 | A1 | 6/2011 | Kunz et al. |
| 2011/0152080 | A1 | 6/2011 | Cristau et al. |
| 2013/0079557 | A1 | 3/2013 | Seitz et al. |
| 2015/0201616 | A1 | 7/2015 | Wachendorff-Neumann et al. |
| 2015/0366198 | A1* | 12/2015 | Meng .................. C07D 209/10 514/30 |

FOREIGN PATENT DOCUMENTS

| WO | 2000/046184 A1 | 8/2000 |
| WO | 2003/024219 A1 | 3/2003 |
| WO | 2003/093224 A1 | 11/2003 |
| WO | 2004/037239 A1 | 5/2004 |
| WO | 2005/089547 A1 | 9/2005 |
| WO | 2005/120234 A2 | 12/2005 |
| WO | 2007/031507 A2 | 3/2007 |
| WO | 2007/031508 A1 | 3/2007 |
| WO | 2007/031512 A2 | 3/2007 |
| WO | 2007/031513 A1 | 3/2007 |
| WO | 2007/031523 A1 | 3/2007 |
| WO | 2007/031524 A1 | 3/2007 |
| WO | 2007/031526 A1 | 3/2007 |
| WO | 2007/031527 A1 | 3/2007 |
| WO | 2007/061966 A2 | 5/2007 |
| WO | 2007/093227 A1 | 8/2007 |
| WO | 2008/101682 A2 | 8/2008 |
| WO | 2008/110278 A2 | 9/2008 |

(Continued)

OTHER PUBLICATIONS

XP002750912, Database Registry [Online] Chemical Abstracts Service, Columbus, Ohio, US; 2 (Aug. 6, 2001), Database accession No. 350509-38-5.

(Continued)

*Primary Examiner* — Samantha L Shterengarts
(74) *Attorney, Agent, or Firm* — McBee Moore Woodward & Vanik IP, LLC

(57) ABSTRACT

The present invention relates to halogen-substituted phenoxyphenylamidines of the general formula (I), to a process for their preparation, to the use of the amidines according to the invention for controlling unwanted microorganisms and also to an agrochemical formulation for this purpose, comprising the halogen-substituted phenoxyphenylamidines according to the invention. Furthermore, the invention relates to a method for controlling unwanted microorganisms by applying the compounds according to the invention to the microorganisms and/or their habitat.

20 Claims, No Drawings

(56) References Cited

FOREIGN PATENT DOCUMENTS

| WO | 2008/110279 A1 | 9/2008 |
| WO | 2008/110280 A2 | 9/2008 |
| WO | 2008/110312 A1 | 9/2008 |
| WO | 2008/110313 A1 | 9/2008 |
| WO | 2008/110315 A1 | 9/2008 |
| WO | 2008/113017 A1 | 9/2008 |
| WO | 2008110281 A2 | 9/2008 |
| WO | 2008/128639 A1 | 10/2008 |
| WO | 2009/0156074 A2 | 12/2009 |
| WO | 2009/156098 A2 | 12/2009 |
| WO | 2010/086118 A1 | 8/2010 |
| WO | 2012/025450 A1 | 3/2012 |
| WO | 2012/090969 A1 | 7/2012 |
| WO | 2012/146125 A1 | 11/2012 |
| WO | 2013/136275 A1 | 9/2013 |
| WO | 2014/037314 A2 | 3/2014 |
| WO | 2014/157596 A1 | 10/2014 |

OTHER PUBLICATIONS

International Search Report of PCT/EP2016/063254 dated Aug. 19, 2016.

\* cited by examiner

HALOGEN-SUBSTITUTED PHENOXYPHENYLAMIDINES AND THE USE THEREOF AS FUNGICIDES

CROSS-REFERENCE TO RELATED APPLICATIONS

This application is a National Stage entry of International Application No. PCT/EP2016/063254, filed Jun. 10, 2016, which claims priority to European Patent Application No. 15172106.5, filed Jun. 15, 2015.

BACKGROUND

Field

The present invention relates to halogen-substituted phenoxyphenylamidines of the general formula (I), to a process for their preparation, to the use of the amidines according to the invention for controlling unwanted microorganisms and also to a composition for this purpose, comprising the halogen-substituted phenoxyphenylamidines according to the invention. Furthermore, the invention also relates to a method for controlling unwanted microorganisms, characterized in that the compounds of the formula (I) are applied to the microorganisms and/or in their habitat.

Description of Related Art

WO2000/046184 discloses the use of amidines, including N-methyl-N-methyl-N'-[(4-phenoxy)-2,5-xylyl]-formamidine, as fungicides.

WO2003/093224, WO2007/031512, WO2007/031513, WO2007/031523, WO2007/031524, WO2007/031526, WO2007/031527, WO2007/061966, WO2008/101682, WO2008/110279, WO2008/110280, WO2008/110281, WO2008/110312, WO2008/110313, WO2008/110314, WO2008/110315, WO2008/128639, WO2009/156098, WO2009/156074, WO2010/086118, WO2012/025450, WO2012/090969 and WO2014/157596 disclose the use of arylamidine derivatives as fungicides.

WO2007/031508 and WO2007/093227 disclose the use of arylamidine derivatives as fungicides and insecticides.

WO2003/024219 discloses fungicide compositions comprising at least one N2-phenylamidine derivative in combination with a further selected known active compound.

WO2004/037239 discloses antifungicidal medicaments based on N2-phenylamidine derivatives.

WO2005/089547, WO2005/120234, WO2012/146125, WO2013/136275, and WO2014/037314 disclose fungicide mixtures comprising at least one arylamidine derivative and a further selected known fungicide.

WO2007/031507 discloses fungicide mixtures comprising at least one arylamidine derivative and two other selected known fungicides.

From WO2008/110278 it is known that various phenylamidine derivatives exhibit fungicidal properties. It is further mentioned that compounds according to formula (I) disclosed in WO2008/110278 possess outstanding herbicidal properties. Herbicides are substances used to control or eliminate unwanted plants (weeds), i.e. they have in general plant destructive properties used in agriculture to eliminate weeds in crop production fields. One can distinguish between selective and non-selective herbicides. The first encompass compounds capable of eliminating specific target weeds while leaving the desired crop relatively unharmed. In contrast, once they are applied, compounds of the second class kill all living plant material. WO2008/110278 indicates that compounds according to formula (I) of WO2008/110278 have a selective herbicidal activity against weeds but leave crops such as wheat, barley, rye, maize, sugar beet, cotton and soybean relatively undamaged. However, the biological examples disclosed in WO2008/110278 rather indicate that certain compounds according to formula (I) of WO2008/110278 possess herbicidal properties against some weeds to a certain extent (at least 80% herbicidal activity assessed via visibility of damage of the treated plants) without indicating which crop plants (such as the ones mentioned above) were used to prove herbicidal selectivity leaving treated crops unharmed. Furthermore, the rate of damage of the tested (but not specified) crops was not indicated. Additionally it is known that different cultivars of a certain crop exhibit different sensitivity levels towards a certain herbicidal active compound. Especially in view of this fact, the statement of WO2008/110278 that the above-mentioned crops are not or only slightly damaged after treatment with compounds according to formula (I) of WO2008/110278 is rather very general.

Concluding, the herbicidal selectivity of the compounds disclosed in WO2008/110278 is questionable. Therefore the potential damage to crops caused by compounds from WO2008/110278 is unforeseeable.

The effectiveness of the amidines described in the prior art as fungicides is good but in many cases leaves something to be desired.

SUMMARY

Accordingly, it is an object of the present invention to provide amidines having an improved fungicidal effectiveness and to improve the compatibility with plants.

A further issue to consider when developing new and improved phenylamidines as fungicides is an improved chemical stability of such compounds compared to known amidines e.g. increased stability towards hydrolysis and/or photolysis.

Generally, hydrolysis means a reaction with water. It is a chemical process in which one or more chemical bonds in a molecule are cleaved by the addition of water. Sometimes this addition causes the split of this molecule into two parts. As a result, hydrolysis of a molecule leads to significant changes of the architecture of this molecule resulting in a different interaction potential of the molecule with enzymes or other proteins. As a consequence, hydrolytic processes usually have a significant impact on the biological activity of a substance including its fungicidal activity typically leading to a loss of biological and fungicidal activity respectively.

The chemical stability towards hydrolysis of the amidines described in the prior art is good but an improved stability may be an advantage during the preparation and formulation processes in a large scale.

Accordingly, it is another object of the present invention to provide amidines having an improved chemical stability towards hydrolysis.

Photolysis, which is also known as photodegradation, photodissociation or photodecomposition, is a chemical process in which a chemical molecule is broken down into smaller units through the absorption of light, i.e. photons. As a result, photolysis of a molecule leads to significant changes of the architecture of this molecule resulting in a different interaction potential of this molecule with enzymes or other proteins. As a consequence, photolytic processes usually have a significant impact on the biological activity of a substance including its fungicidal activity typically leading to a loss of biological and fungicidal activity respectively. It is known that photodegradation is an important abiotic disappearance pathway for pesticides, including fungicides (see Tsao and Eto, Agric. Biol. Chem., 55 (3), 763-768, 1991).

The stability towards photolysis of the amidines described in the prior art is good but an improved stability may be an advantage as it could offer a longer lasting efficacy when applied to plants by foliar application.

Accordingly, it is another object of the present invention to provide amidines having an improved stability towards photolysis.

Surprisingly, these objects have been achieved by halogen-substituted phenoxyphenylamidines of the formula (I)

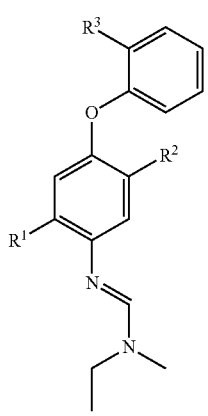

in which

R$^1$ is methyl;

R$^2$ is selected from the group consisting of halogen and halomethyl;

R$^3$ is halogen.

The radical definitions specified above can be combined with one another as desired.

According to the type of substituents defined above, the compounds of the formula (I) have basic properties and can form salts, possibly also internal salts or adducts, with inorganic or organic acids or with metal ions. The compounds of the formula (I) carry amidine groups which induce basic properties. Thus, these compounds can be reacted with acids to give salts, or they are obtained directly as salts by the synthesis.

DETAILED DESCRIPTION OF A PREFERRED EMBODIMENT

The salts obtainable in this way likewise have fungicidal properties.

Examples of inorganic acids are hydrohalic acids, such as hydrogen fluoride, hydrogen chloride, hydrogen bromide and hydrogen iodide, sulphuric acid, phosphoric acid and nitric acid, and acidic salts, such as NaHSO$_4$ and KHSO$_4$. As organic acids come, for example, formic acid, carbonic acid and alkanoic acids such as acetic acid, trifluoroacetic acid, trichloroacetic acid and propionic acid, and also glycolic acid, thiocyanic acid, lactic acid, succinic acid, citric acid, benzoic acid, cinnamic acid, oxalic acid, saturated or mono- or diunsaturated C$_6$-C$_{20}$ fatty acids, alkylsulphonic acids (sulphonic acids having straight-chain or branched alkyl radicals having 1 to 20 carbon atoms), arylsulphonic acids or aryldisulphonic acids (aromatic radicals, such as phenyl and naphthyl, which bear one or two sulphonic acid groups), alkylphosphonic acids (phosphonic acids having straight-chain or branched alkyl radicals having 1 to 20 carbon atoms), arylphosphonic acids or aryldiphosphonic acids (aromatic radicals, such as phenyl and naphthyl, which bear one or two phosphonic acid radicals), where the alkyl and aryl radicals may bear further substituents, for example p-toluenesulphonic acid, salicylic acid, p-aminosalicylic acid, 2-phenoxybenzoic acid, 2-acetoxybenzoic acid, etc.

Useful metal ions are especially the ions of the elements of the second main group, especially calcium and magnesium, of the third and fourth main group, especially aluminum and tin, and also of the first to eighth transition groups, especially manganese, iron, cobalt, nickel, copper, zinc and others. Particular preference is given to the metal ions of the elements of the fourth period. The metals may be present in the different valences that they can assume.

Optionally substituted groups may be mono- or polysubstituted, where the substituents in the case of polysubstitutions may be the same or different.

The present invention furthermore provides a process for preparing the phenoxyphenylamidines according to the invention which comprises at least one of the following steps (a) to (j):

(a) reaction of nitrobenzene derivatives of the formula (III) with phenol derivatives of the formula (II) according to the reaction scheme below:

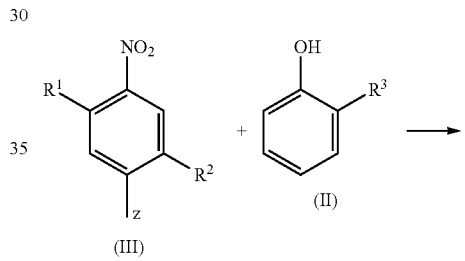

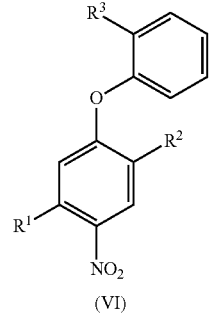

(b) reaction of nitrophenol derivatives of the formula (V) with phenyl derivatives of the formula (IV) according to the reaction scheme below:

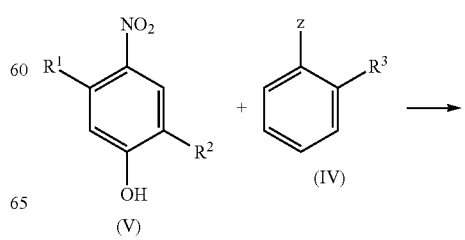

-continued

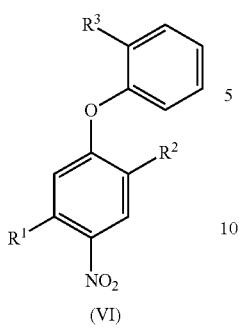

(VI)

(c) reaction of anilines of the formula (VII) with phenol derivatives of the formula (II) according to the reaction scheme below:

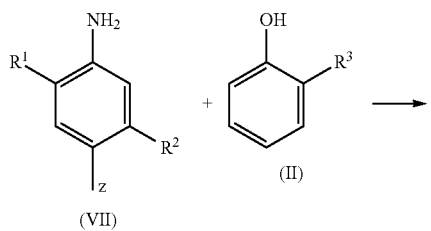

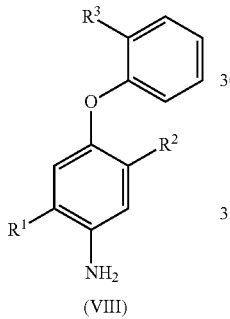

(VIII)

(d) reaction of aminophenols of the formula (XII) with phenyl derivatives of the formula (IV) according to the reaction scheme below:

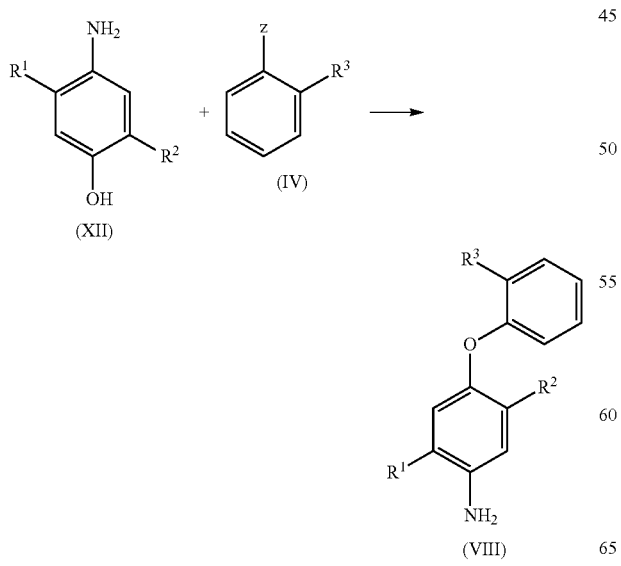

(e) reduction of the nitrophenyl ethers of the formula (VI) to aminophenyl ethers of the formula (VIII) according to the reaction scheme below:

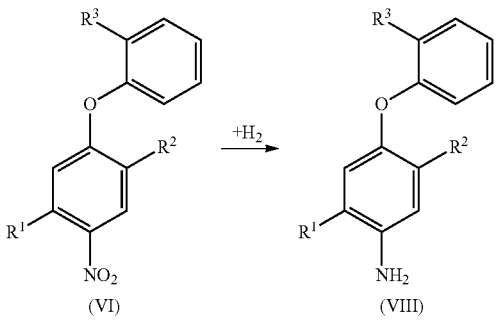

(f) reaction of the aminophenyl ethers of the formula (VIII) with
  (i) aminoacetals of the formula (XIII) or
  (ii) with N-ethyl-N-methylformamide of the formula (XIV) or
  (iii) with N-methylethanamine of the formula (XV) in the presence of ortho esters of the formula (XVI)
according to the reaction scheme below:

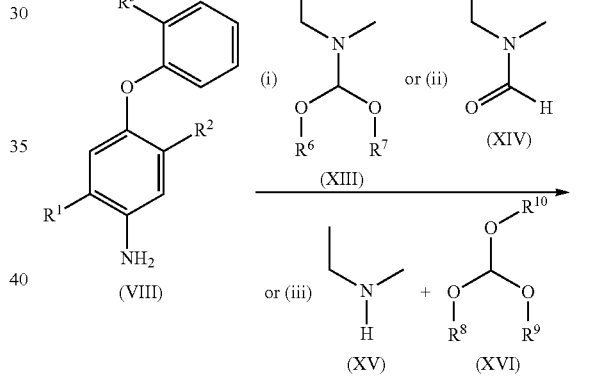

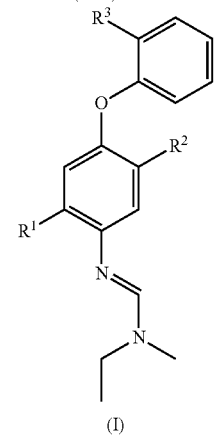

(I)

(g) reaction of the aminophenols of the formula (XII) with
  (i) aminoacetals of the formula (XIII) or
  (ii) with N-ethyl-N-methylformamide of the formula (XIV) or
  (iii) with N-methylethanamine of the formula (XV) in the presence of ortho esters of the formula (XVI)

according to the reaction scheme below:

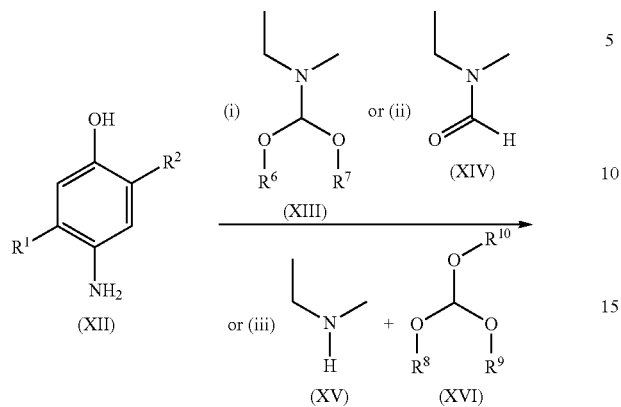

(h) reaction of the anilines of the formula (VII) with
  (i) aminoacetals of the formula (XIII) or
  (ii) with N-ethyl-N-methylformamide of the formula (XIV) or
  (iii) with N-methylethanamine of the formula (XV) in the presence of ortho esters of the formula (XVI) according to the reaction scheme below:

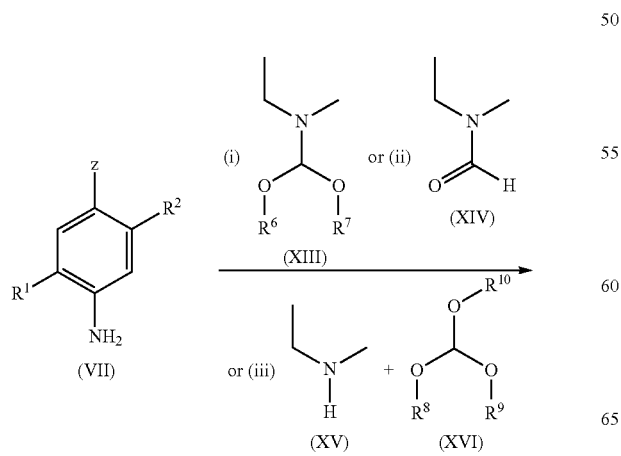

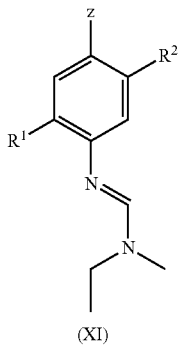

(i) reaction of amidines of the formula (XI) with phenol derivatives of the formula (II) according to the reaction scheme below:

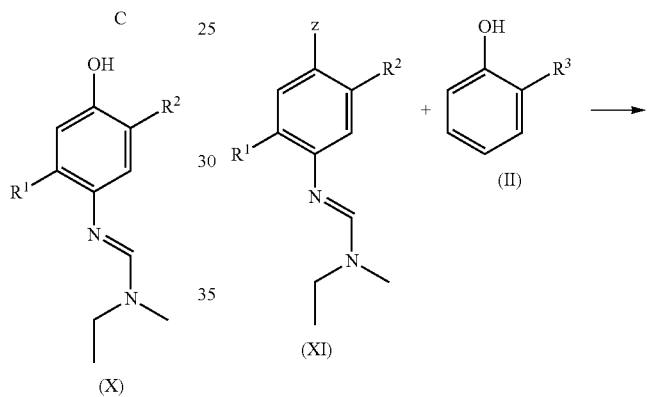

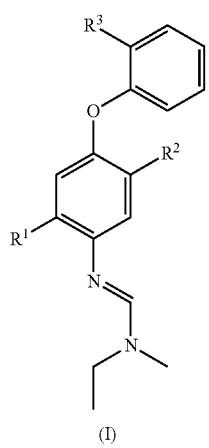

(j) reaction of amidines of the formula (X) with phenyl derivatives of the formula (IV) according to the reaction scheme below:

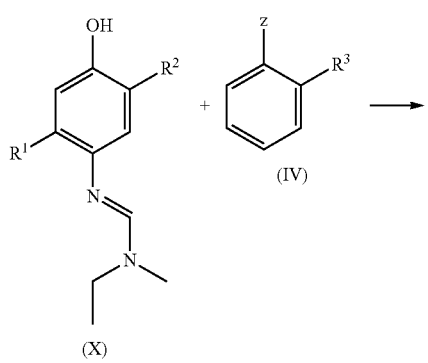

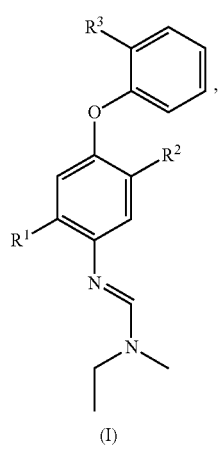

where in the above schemes
Z is a leaving group;
$R^1$ to $R^3$ have the above meanings;
$R^6$ and $R^7$ independently of one another are selected from the group consisting of $C_{1-12}$-alkyl, $C_{2-12}$-alkenyl, $C_{2-12}$-alkynyl or $C_{5-18}$-aryl or $C_{7-19}$-arylalkyl groups and together with the atoms to which they are attached may form a five-, six- or seven-membered ring;
$R^8$ to $R^{10}$ independently of one another are selected from the group consisting of $C_{1-12}$-alkyl, $C_{2-12}$-alkenyl, $C_{2-12}$-alkynyl or $C_{5-18}$-aryl or $C_{7-19}$-arylalkyl, $C_{7-19}$-alkylaryl groups and in each case $R^8$ with $R^9$, $R^9$ with $R^{10}$ or $R^8$ with $R^{10}$ together with the atoms to which they are attached and if appropriate together with further carbon, nitrogen, oxygen or sulfur atoms may form a five-, six- or seven-membered ring.

A third subject matter of the invention is the use of the halogen-substituted phenoxyphenylamidines according to the invention or of agrochemical formulations comprising these for controlling unwanted microorganisms.

A fourth subject matter of the present invention is an agrochemical formulation for controlling unwanted microorganisms, comprising at least one halogen-substituted phenoxyphenylamidines according to the present invention.

A further subject matter of the invention relates to a method for controlling unwanted microorganisms, characterized in that the halogen-substituted phenoxyphenylamidines according to the invention or agrochemical formulations comprising these are applied to the microorganisms and/or their habitat.

Moreover, the invention further relates to seed which has been treated with at least one compound of the formula (I).

The invention finally provides a method for protecting seed against unwanted microorganisms by using seed treated with at least one compound of the formula (I).

General Definitions

In connection with the present invention, the term halogens (X) comprises, unless otherwise defined, those elements which are chosen from the group consisting of fluorine, chlorine, bromine and iodine, where fluorine, chlorine and bromine are preferably used and fluorine and chlorine are particularly preferably used.

Optionally substituted groups can be mono- or polysubstituted, where in the case of polysubstitution the substituents can be identical or different.

In the definitions of the symbols given in the above formulae, collective terms were used, which are generally representative of the following substituents:

Halogen: fluorine, chlorine, bromine and iodine and preferably fluorine, chlorine, bromine and more preferably fluorine, chlorine.

Halomethyl: a methyl group, where some or all of the hydrogen atoms in these groups may be replaced by halogen atoms as specified above, for example (but not limited to) chloromethyl, bromomethyl, dichloromethyl, trichloromethyl, fluoromethyl, difluoromethyl, trifluoromethyl, chlorofluoromethyl, dichlorofluoromethyl, chlorodifluoromethyl.

Not included are combinations which are contrary to natural laws and which the person skilled in the art, based on his expert knowledge, would thus have excluded Depending on the nature of the substituents, the compounds of the formula (I) may be in the form of geometric and/or optically active isomers or corresponding isomer mixtures in different compositions. These stereoisomers are, for example, diastereomers, atropisomers or geometric isomers. Accordingly, the invention encompasses both pure stereoisomers and any mixture of these isomers.

The halogen-substituted phenoxyphenylamidines according to the invention are compounds of the formula (I)

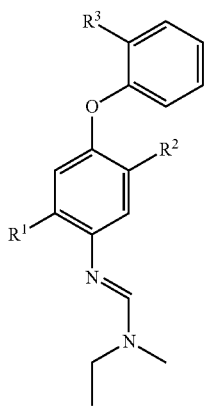

or their salts, N-oxides, metal complexes and their stereoisomers.

In the formula (I), the groups have the meanings defined below. The given definitions also apply to all intermediates:
$R^1$ is methyl;
$R^2$ is selected from the group consisting of halogen and halomethyl;
$R^3$ is halogen.

In an alternative embodiment the groups in formula (I), have the meanings defined below. The definitions likewise apply to all intermediates:
$R^1$ is methyl;
$R^2$ is halogen;
$R^3$ is halogen.

In a further alternative embodiment the groups in formula (I), have the meanings defined below. The definitions likewise apply to all intermediates:
$R^1$ is methyl;
$R^2$ is halomethyl;
$R^3$ is halogen.

In formula (I), the groups have the preferred meanings defined below. The definitions given as being preferred likewise apply to all intermediates:
$R^1$ is preferably methyl;
$R^2$ is preferably selected from the group consisting of fluoro, chloro, bromo, dichloromethyl, trichloromethyl, fluoromethyl, difluoromethyl, and trifluoromethyl;
$R^3$ is preferably selected from the group consisting of bromo, chloro and fluoro.

In the formula (I), the radicals have the particularly preferred meanings defined below. The definitions given as being particularly preferred likewise apply to all intermediates:
$R^1$ is particularly preferably methyl;
$R^2$ is particularly preferably selected from the group consisting of chloro, bromo, difluoromethyl, and trifluoromethyl;
$R^3$ is particularly preferably fluoro, chloro, bromo, and iodo.

In an alternative embodiment the groups in formula (I), have particularly preferred the meanings defined below. The definitions given as being particularly preferred likewise apply to all intermediates:
$R^1$ is particularly preferably methyl;
$R^2$ is particularly preferably chloro, bromo;
$R^3$ is particularly preferably fluoro, chloro, bromo, and iodo.

In a further alternative embodiment the groups in formula (I), have particularly preferred the meanings defined below. The definitions given as being particularly preferred likewise apply to all intermediates:
$R^1$ is particularly preferably methyl;
$R^2$ is particularly preferably difluoromethyl, and trifluoromethyl;
$R^3$ is particularly preferably fluoro, chloro, bromo, and iodo.

Phenoxyphenylamidines preferred in connection with the present invention are selected from the group consisting of: (I-01) N'-[5-chloro-4-(2-fluorophenoxy)-2-methylphenyl]-N-ethyl-N-methylimidoformamide, (I-02) N'-[4-(2-bromophenoxy)-5-chloro-2-methylphenyl]-N-ethyl-N-methylimidoformamide, (I-03) N'-[5-chloro-4-(2-chlorophenoxy)-2-methylphenyl]-N-ethyl-N-methylimidoformamide, (I-04) N-ethyl-N'-[4-(2-fluorophenoxy)-2-methyl-5-(trifluoromethyl)phenyl]-N-methylimidoformamide, (I-05) N'-[4-(2-bromophenoxy)-2-methyl-5-(trifluoromethyl)phenyl]-N-ethyl-N-methylimidoformamide, (I-06) N'-[5-chloro-4-(2-iodophenoxy)-2-methylphenyl]-N-ethyl-N-methylimidoformamide.

Phenoxyphenylamidines particularly preferred in connection with the present invention are selected from the group consisting of: (I-01) N'-[5-chloro-4-(2-fluorophenoxy)-2-methylphenyl]-N-ethyl-N-methylimidoformamide, (I-02) N'-[4-(2-bromophenoxy)-5-chloro-2-methylphenyl]-N-ethyl-N-methylimidoformamide.

The compounds of the formula (I) carry amidine groups which induce basic properties. Thus, these compounds can be reacted with acids to give salts.

Examples of inorganic acids are hydrohalic acids, such as hydrogen fluoride, hydrogen chloride, hydrogen bromide and hydrogen iodide, sulfuric acid, phosphoric acid and nitric acid, and acidic salts, such as $NaHSO_4$ and $KHSO_4$.

Suitable organic acids are, for example, formic acid, carbonic acid and alkanoic acids, such as acetic acid, trifluoroacetic acid, trichloroacetic acid and propionic acid, and also glycolic acid, thiocyanic acid, lactic acid, succinic acid, citric acid, benzoic acid, cinnamic acid, oxalic acid, alkylsulfonic acids (sulfonic acids having straight-chain or branched alkyl groups having 1 to 20 carbon atoms), arylsulfonic acids or -disulfonic acids (aromatic groups, such as phenyl and naphthyl, which carry one or two sulfonic acid groups), alkylphosphonic acids (phosphonic acids having straight-chain or branched alkyl groups having 1 to 20 carbon atoms), arylphosphonic acids or -diphosphonic acids (aromatic radicals, such as phenyl and naphthyl, which carry one or two phosphonic acid groups), where the alkyl and aryl groups may carry further substituents, for example p-toluenesulfonic acid, salicylic acid, p-aminosalicylic acid, 2-phenoxybenzoic acid, 2-acetoxybenzoic acid, etc.

The salts obtainable in this manner also have fungicidal properties.

Preparation of the Amidines According to the Invention

The amidines according to the invention can be obtained by the process shown in scheme (I) below:

Scheme (I)

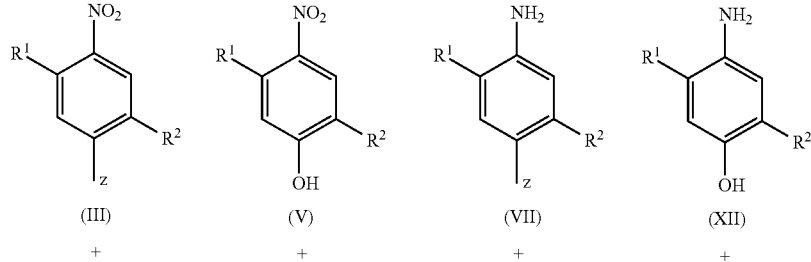

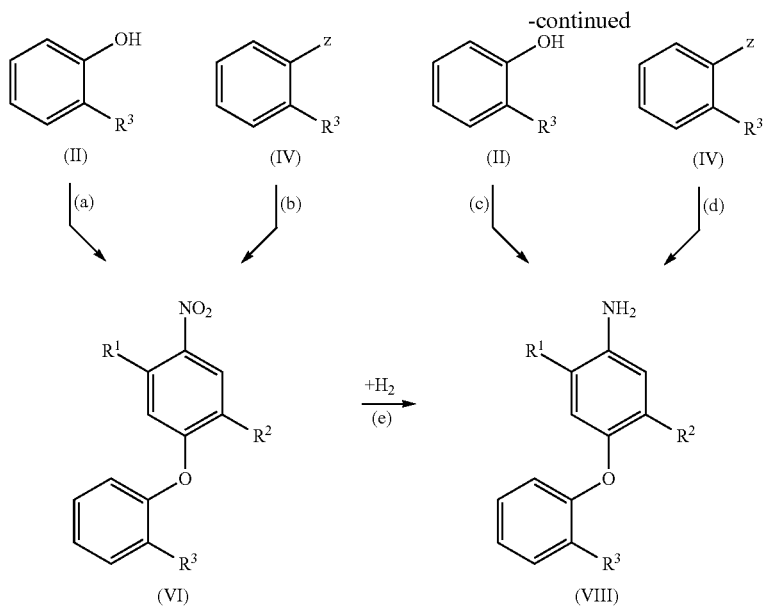
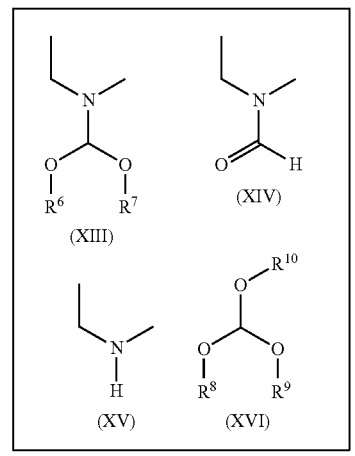
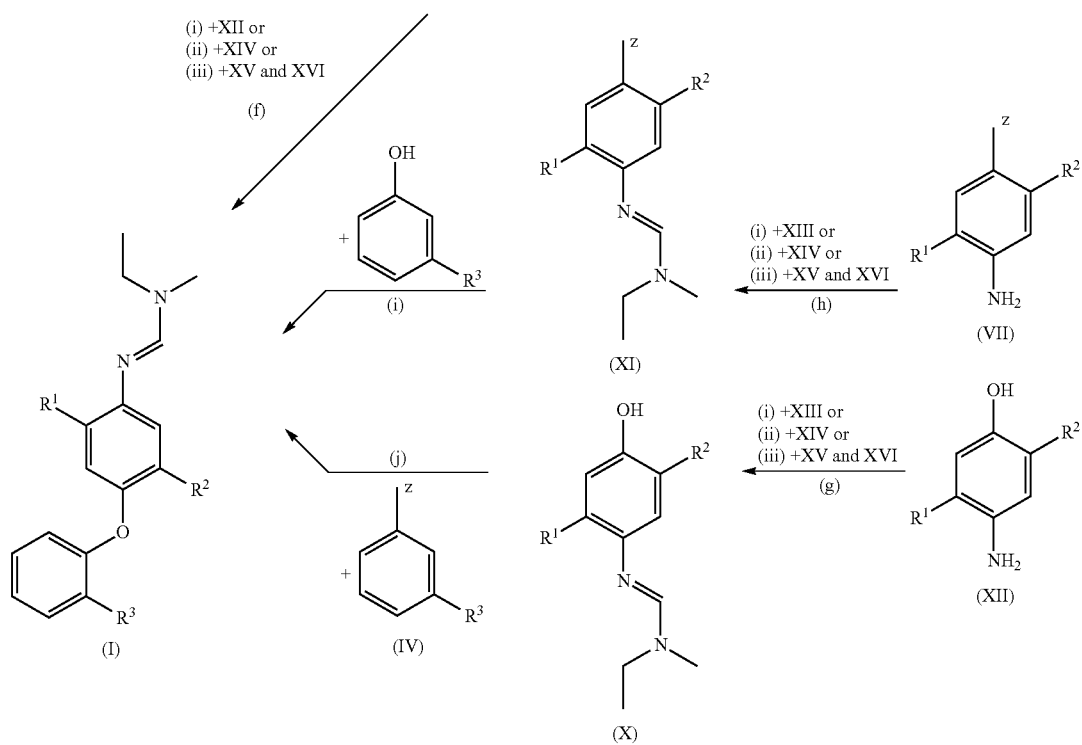

Step (a)

In one embodiment according to the invention, nitrobenzene derivatives of the formula (III) are reacted with phenol derivatives of the formula (II) or the phenoxides formed therefrom in accordance with the reaction scheme below to give nitroaromatics of the formula (VI):

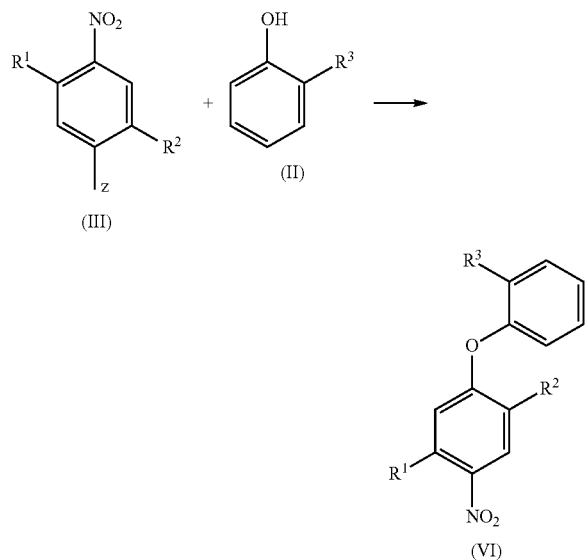

Suitable leaving groups (Z) are all substituents having sufficient nucleofugicity under the prevailing reaction conditions. Examples of suitable leaving groups to be mentioned are halogens, triflate, mesylate, tosylate or $SO_2Me$.

Novel compounds are those of the formula (VI), in which the symbols $R^1$ and $R^3$ have the above-specified general, preferred, or particularly preferred definitions and $R^2$ is selected from the group consisting of chloro, bromo, iodo and halomethyl.

Novel compounds are also those of the formula (VI), in which the symbols $R^1$ and $R^2$ have the above-specified general, preferred, or particularly preferred definitions and $R^3$ is selected from the group consisting of chloro, bromo, iodo and halomethyl.

In the context of the present invention those nitrophenyl ethers of the formula (VI) having the following combinations of $R^1$, $R^2$ and $R^3$ described in Table I-a are particularly preferred.

TABLE I-a

| No. | $R^1$ | $R^2$ | $R^3$ |
|---|---|---|---|
| (VI-01) | Me | Cl | F |
| (VI-02) | Me | Cl | Br |
| (VI-03) | Me | Cl | Cl |
| (VI-04) | Me | CF3 | F |
| (VI-05) | Me | CF3 | Br |
| (VI-06) | Me | Cl | I |

In the context of the present invention those nitrophenyl ethers of the formula (VI) having the following combinations of $R^1$, $R^2$ and $R^3$ described in Table I-b are particularly preferred.

TABLE I-b

| No. | $R^1$ | $R^2$ | $R^3$ |
|---|---|---|---|
| (VI-07) | Me | F | F |

The reaction is preferably carried out in the presence of a base.

Suitable bases are organic and inorganic bases which are usually used in such reactions. Preference is given to using bases which, for example, are selected from the group consisting of hydrides, hydroxides, amides, alkoxides, acetates, fluorides, phosphates, carbonates and bicarbonates of alkali metals or alkaline earth metals. Particular preference is given here to sodium amide, sodium hydride, lithium diisopropylamide, sodium methoxide, potassium tert-butoxide, sodium hydroxide, potassium hydroxide, sodium acetate, sodium phosphate, potassium phosphate, potassium fluoride, cesium fluoride, sodium carbonate, potassium carbonate, potassium bicarbonate, sodium bicarbonate and cesium carbonate. Furthermore, tertiary amines, such as, for example, trimethylamine, triethylamine, tributylamine, N,N-dimethylaniline, N,N-dimethylbenzylamine, pyridine, N-methylpiperidine, N-methylpyrrolidone, N,N-dimethylaminopyridine, diazabicyclooctane (DABCO), diazabicyclononene (DBN) and diazabicycloundecene (DBU).

If appropriate, a catalyst chosen from the group consisting of palladium, copper and their salts or complexes may be used.

The reaction of the nitrobenzene derivative with the phenol derivative can be carried out neat or in a solvent; preferably, the reaction is carried out in a solvent selected from standard solvents which are inert under the prevailing reaction conditions.

Preference is given to aliphatic, alicyclic or aromatic hydrocarbons, such as, for example, petroleum ether, hexane, heptane, cyclohexane, methylcyclohexane, benzene, toluene, xylene or decalin; halogenated hydrocarbons, such as, for example, chlorobenzene, dichlorobenzene, dichloromethane, chloroform, carbon tetrachloride, dichloroethane or trichloroethane; ethers, such as, for example, diethyl ether, diisopropyl ether, methyl tert-butyl ether (MTBE), methyl tert-amyl ether, dioxane, tetrahydrofuran, 1,2-dimethoxyethane, 1,2-diethoxyethane or anisole; nitriles, such as, for example, acetonitrile, propionitrile, n- or isobutyronitrile or benzonitrile; amides, such as, for example, N,N-dimethylformamide (DMF), N,N-dimethylacetamide, N-methylformanilide, N-methylpyrrolidone (NMP) or hexamethylenephosphoric triamide; or mixtures of these with water, and also pure water.

The reaction can be carried out under reduced pressure, at atmospheric pressure or under superatmospheric pressure and at temperatures of from −20 to 200° C.; preferably, the reaction is carried out at atmospheric pressure and temperatures of from 50 to 150° C.

The nitrobenzene derivatives of the formula (III) are commercially available or can be prepared from commercially available precursors by methods described in the literature (for example WO2008/110314).

The phenol derivatives of the formula (II) are commercially available.

Step (b)

In an alternative embodiment according to the invention, nitrophenol derivatives of the formula (V) or the phenoxides formed therefrom are reacted with phenyl derivatives of the formula (IV) in accordance with the reaction scheme below to give nitrophenyl ethers of the formula (VI):

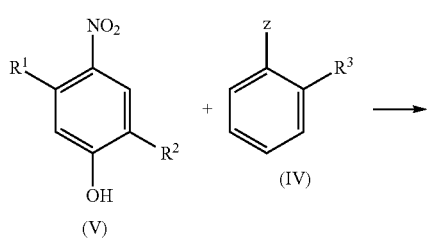

Novel compounds are those of the formula (VIII), in which the symbols $R^1$, $R^2$ and $R^3$ have the above-specified general, preferred, or particularly preferred definitions.

In the context of the present invention those aminophenyl ethers of the formula (VIII) having the following combinations of $R^1$, $R^2$ and $R^3$ described in Table II are particularly preferred.

TABLE II

| No. | $R^1$ | $R^2$ | $R^3$ |
| --- | --- | --- | --- |
| (VIII-01) | Me | Cl | F |
| (VIII-02) | Me | Cl | Br |
| (VIII-03) | Me | Cl | Cl |
| (VIII-04) | Me | CF3 | F |
| (VIII-05) | Me | CF3 | Br |
| (VIII-06) | Me | Cl | I |

The aniline derivatives of the formula (VII) are commercially available or can be prepared from commercially available precursors by methods described in the literature (for example from corresponding nitrobenzene derivatives of the formula (III) by reduction reaction: Bioorganic & Medicinal Chemistry Letters, 16(2), 457-460; 2006).

The phenol derivatives of the formula (II) are commercially available.

Step (a)

In a further alternative embodiment according to the invention, aminophenols of the formula (XII) are reacted with phenyl derivatives of the formula (IV) in accordance with the reaction scheme below to give aminophenyl ethers of the formula (VIII):

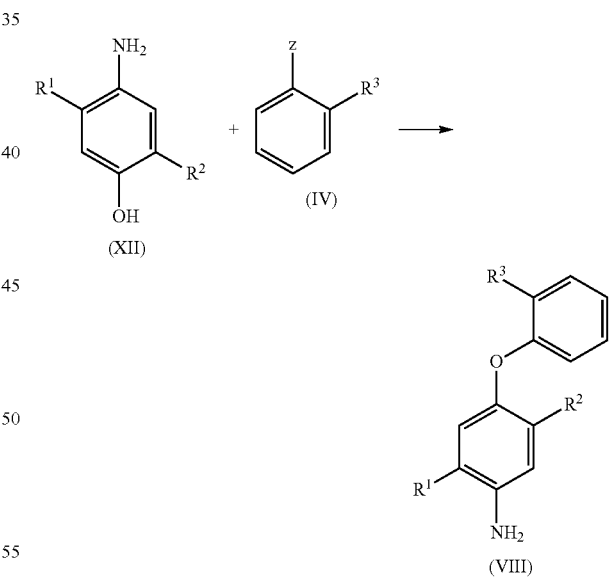

With regard to the reaction conditions, the solvents, the catalysts, the substitution patterns of the nitrophenyl ether (VI) and the suitable leaving groups, reference may be made to step (a).

The nitrophenol derivatives of the formula (V) are commercially available or can be prepared from commercially available precursors by methods described in the literature (for example from corresponding nitrophenol derivatives by halogenation reaction: WO2009/140624).

The phenyl derivatives of the formula (IV) are commercially available.

Step (c)

In a further alternative embodiment according to the invention, aniline derivatives of the formula (VII) are reacted with phenol derivatives of the formula (II) or the phenoxides formed therefrom in accordance with the reaction scheme below to give aminophenyl ethers of the formula (VIII):

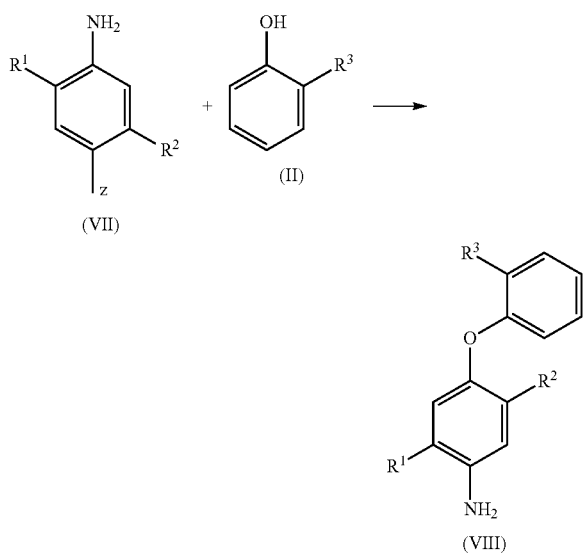

With regard to the reaction conditions, the solvents, the catalysts and the suitable leaving groups, reference may be made to step (a).

With regard to the reaction conditions, the solvents, the catalysts, the substitution patterns of the aminophenyl ether (VIII) and the suitable leaving groups, reference may be made to steps (a) and (c).

Step (e)

The nitrophenyl ethers of the formula (VI) obtained in steps (a) and (b) can be reduced in accordance with the reaction scheme below to give the aminophenyl ethers of the formula (VIII):

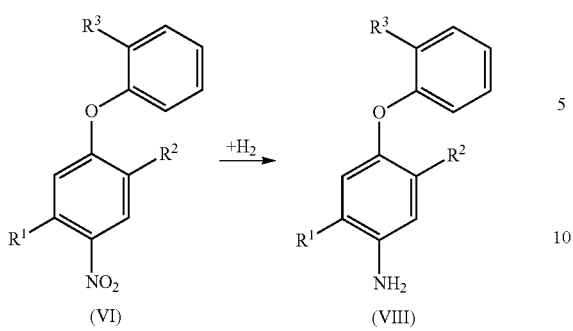

The reduction according to step (e) can be carried out by any methods for reducing nitro groups described in the prior art.

Preferably, the reduction is carried out using tin chloride in concentrated hydrochloric acid, as described in WO2000/46184. However, alternatively, the reduction can also be carried out by using iron in the presence of hydrochloric acid or hydrogen gas, if appropriate in the presence of suitable hydrogenation catalysts, such as, for example, Raney nickel or Pd/C. The reaction conditions have already been described in the prior art and are familiar to the person skilled in the art.

If the reduction is carried out in the liquid phase, the reaction should take place in a solvent inert to the prevailing reaction conditions. One such solvent is, for example, toluene, methanol, or ethanol.

Step (f)

The conversion of the anilines of the formula (VIII) into the amidines of the formula (I) according to the invention according to step (f) can be carried out, as shown above in schema (I), using different alternative methods employing
(i) aminoacetals of the formula (XIII) or
(ii) N-ethyl-N-methylformamide of the formula (XIV) or
(iii) N-methylethanamine of the formula (XV) in the presence of ortho esters of the formula (XVI) according to the reaction scheme below:

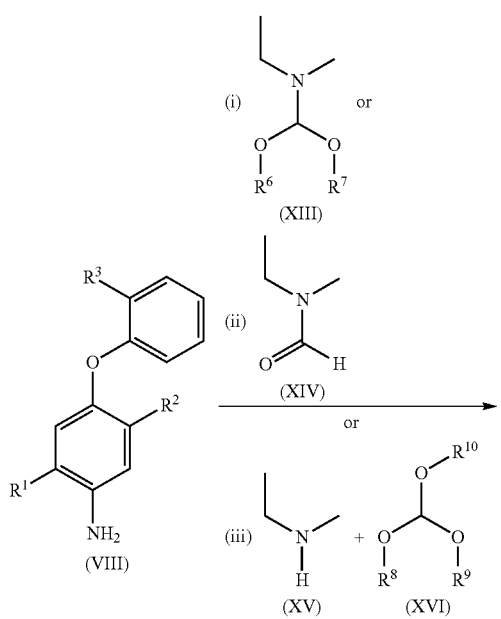

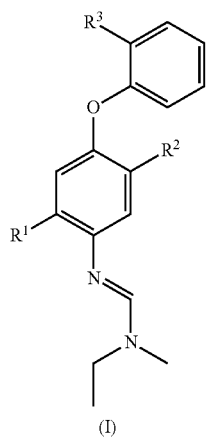

The individual alternative embodiments (i) to (iii) of the process according to the invention are briefly illustrated below:

(i) According to one embodiment according to the invention, shown in scheme (I) as step (i), the aminophenyl ethers of the formula (VIII) are reacted with aminoacetals of the formula (XIII), where $R^6$ and $R^7$ are selected from the group consisting of $C_{1-8}$-alkyl groups, preferably from $C_{1-6}$-alkyl groups, particularly preferably from $C_{1-4}$-alkyl groups and together with the oxygen atoms to which they are attached may form a five- or six-membered ring, to give the halogen-substituted phenoxyphenylamidines of the formula (I) according to the invention.

The aminoacetals of the formula (XIII) can be obtained from the N-ethyl-N-methylformamide described in JACS, 65, 1566 (1943), by reaction with alkylating agents, such as, for example, dimethyl sulfate.

The reaction according to step (i) is preferably carried out in the absence of a base or an acid.

(ii) In an alternative embodiment according to the invention, shown in scheme (I) as step (ii), the aminophenyl ethers of the formula (VIII) are reacted with N-ethyl-N-methylformamide of the formula (XIV) to give the halogen-substituted phenoxyphenylamidines according to the invention.

The reaction according to step (ii) is, if appropriate, carried out in the presence of a halogenating agent. Suitable halogenating agents are, for example, selected from the group consisting of $PCl_5$, $PCl_3$, $POCl_3$ or $SOCl_2$.

Moreover, the reaction may alternatively be carried out in the presence of a condensing agent.

Suitable condensing agents are those usually employed for forming amide bonds; acid halide formers, such as, for example, phosgene, phosphorus tribromide, phosphorus trichloride, phosphorus pentachloride, phosphorus oxytrichloride or thionyl chloride; anhydride formers, such as, for example, chloroformate, methyl chloroformate, isopropyl chloroformate, isobutyl chloroformate or methanesulfonyl chloride; carbodiimines, such as, for example, N,N'-dicyclohexylcarbodiimine (DCC) or other customary condensing agents, such as, for example, phosphorus pentoxide, polyphosphoric acid, N,N'-carbodiimidazole, 2-ethoxy-N-ethoxycarbonyl-1,2-dihydroquinoline (EEDQ), triphenylphosphine/carbon tetrachloride or bromotripyrrolidinophosphonium hexafluorophosphate may be mentioned by way of examples.

The reaction according to step (ii) is preferably carried out in a solvent selected from standard solvents which are inert under the prevailing reaction conditions. Preference is given to aliphatic, alicyclic or aromatic hydrocarbons, such as, for example, petroleum ether, hexane, heptane, cyclohexane, methylcyclohexane, benzene, toluene, xylene or decalin; halogenated hydrocarbons, such as, for example, chlorobenzene, dichlorobenzene, dichloromethane, chloroform, carbon tetrachloride, dichloroethane or trichloroethane; ethers, such as, for example, diethyl ether, diisopropyl ether, methyl tert-butyl ether (MTBE), methyl tert-amyl ether, dioxane, tetrahydrofuran, 1,2-dimethoxyethane, 1,2-diethoxyethane or anisole; nitriles, such as, for example, acetonitrile, propionitrile, n- or isobutyronitrile or benzonitrile; amides, such as, for example, N,N-dimethylformamide (DMF), N,N-dimethylacetamide, N-methylformanilide, N-methylpyrrolidone (NMP) or hexamethylenephosphoric triamide; esters, such as, for example, methyl acetate or ethyl acetate; sulfoxides, such as, for example, dimethyl sulfoxide (DMSO); sulfones, such as, for example, sulfolane; alcohols, such as, for example, methanol, ethanol, n- or isopropanol, n-, iso-, sec- or tert-butanol, ethanediol, propane-1,2-diol, ethoxyethanol, methoxyethanol, diethylene glycol monomethyl ether, diethylene glycol monoethyl ether or mixtures of these.

(iii) According to a further alternative embodiment according to the invention shown in scheme (I) as step (iii), the aminophenyl ethers of the formula (VIII) are reacted with N-methylethanamine of the formula (XV) in the presence of ortho esters of the formula (XVI), in which $R^8$ to $R^{10}$ independently of one another are selected from the group consisting of $C_{1-8}$-alkyl groups, preferably from $C_{2-6}$-alkyl groups, particularly preferably from $C_{3-5}$-alkyl groups and together with the oxygen atoms to which they are attached may form a five- or six-membered ring, to give the halogen-substituted phenoxyphenylamidines according to the invention.

The reaction according to step (iii) is preferably carried out in a solvent selected from standard solvents which are inert under the prevailing reaction conditions. Preference is given to aliphatic, alicyclic or aromatic hydrocarbons, such as, for example, petroleum ether, hexane, heptane, cyclohexane, methylcyclohexane, benzene, toluene, xylene or decalin; halogenated hydrocarbons, such as, for example chlorobenzene, dichlorobenzene, dichloromethane, chloroform, carbon tetrachloride, dichloroethane or trichloroethane; ethers, such as, for example, diethyl ether, diisopropyl ether, methyl tert-butyl ether (MTBE), methyl tert-amyl ether, dioxane, tetrahydrofuran, 1,2-dimethoxyethane, 1,2-diethoxyethane or anisole; nitriles, such as, for example, acetonitrile, propionitrile, n- or isobutyronitrile or benzonitrile; amides, such as, for example, N,N-dimethylformamide (DMF), N,N-dimethylacetamide, N-methylformanilide, N-methylpyrrolidone (NMP) or hexamethylene phosphoric triamide; esters, such as, for example, methyl acetate or ethyl acetate; sulfoxides, such as, for example, dimethyl sulfoxide (DMSO); sulfones, such as, for example, sulfolane; alcohols, such as, for example, methanol, ethanol, n- or isopropanol, n-, iso-, sec- or tert-butanol, ethanediol, propane-1,2-diol, ethoxyethanol, methoxyethanol, diethylene glycol monomethyl ether, diethylene glycol monoethyl ether; or mixtures of these with water, and also pure water.

Step (g)
In an alternative embodiment according to the invention, it is already possible to react the aminophenols of the formula (XII)
(i) with aminoacetals of the formula (XIII) or
(ii) with N-ethyl-N-methylformamide of the formula (XIV) or
(iii) with N-methylethanamine of the formula (XV) in the presence of ortho esters of the formula (XVI)
in accordance with the reaction scheme below to give amidines of the formula (X):

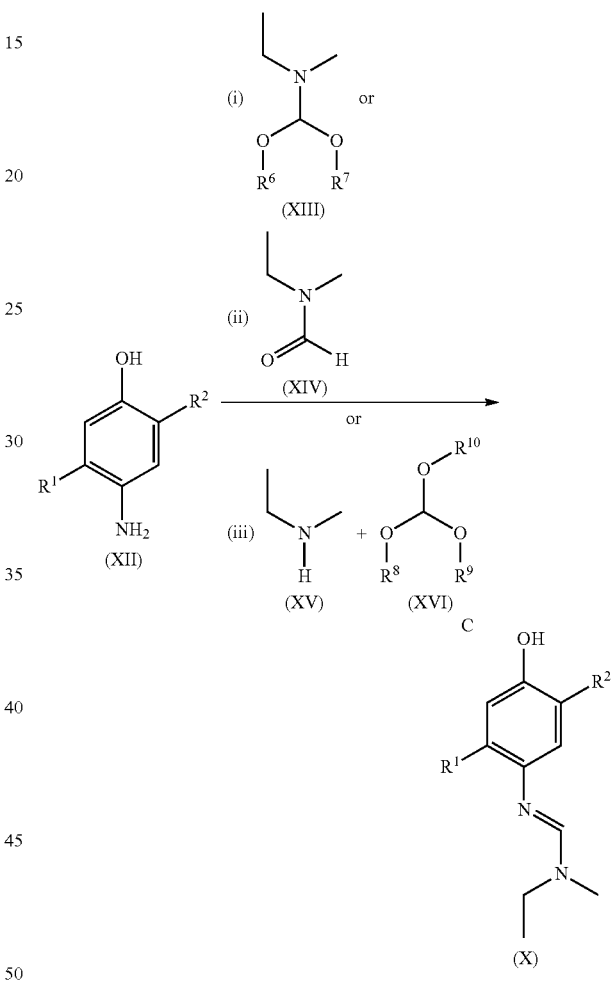

With regard to the reaction conditions, solvents, catalysts and substitution patterns of the amidines (X), reference may be made to step (f) and to Tables I and II.

The further conversion of the amidines of the formula (X) into the target molecules of the formula (I) according to the invention can be carried out, for example, as described in step (j).

Step (h)
In an alternative embodiment according to the invention, it is possible to react the aniline derivatives of the formula (VII)
(i) with aminoacetals of the formula (XIII) or
(ii) with N-ethyl-N-methylformamide of the formula (XIV) or
(iii) with N-methylethanamine of the formula (XV) in the presence of ortho esters of the formula (XVI)

in accordance with the reaction scheme below to give amidines of the formula (XI):

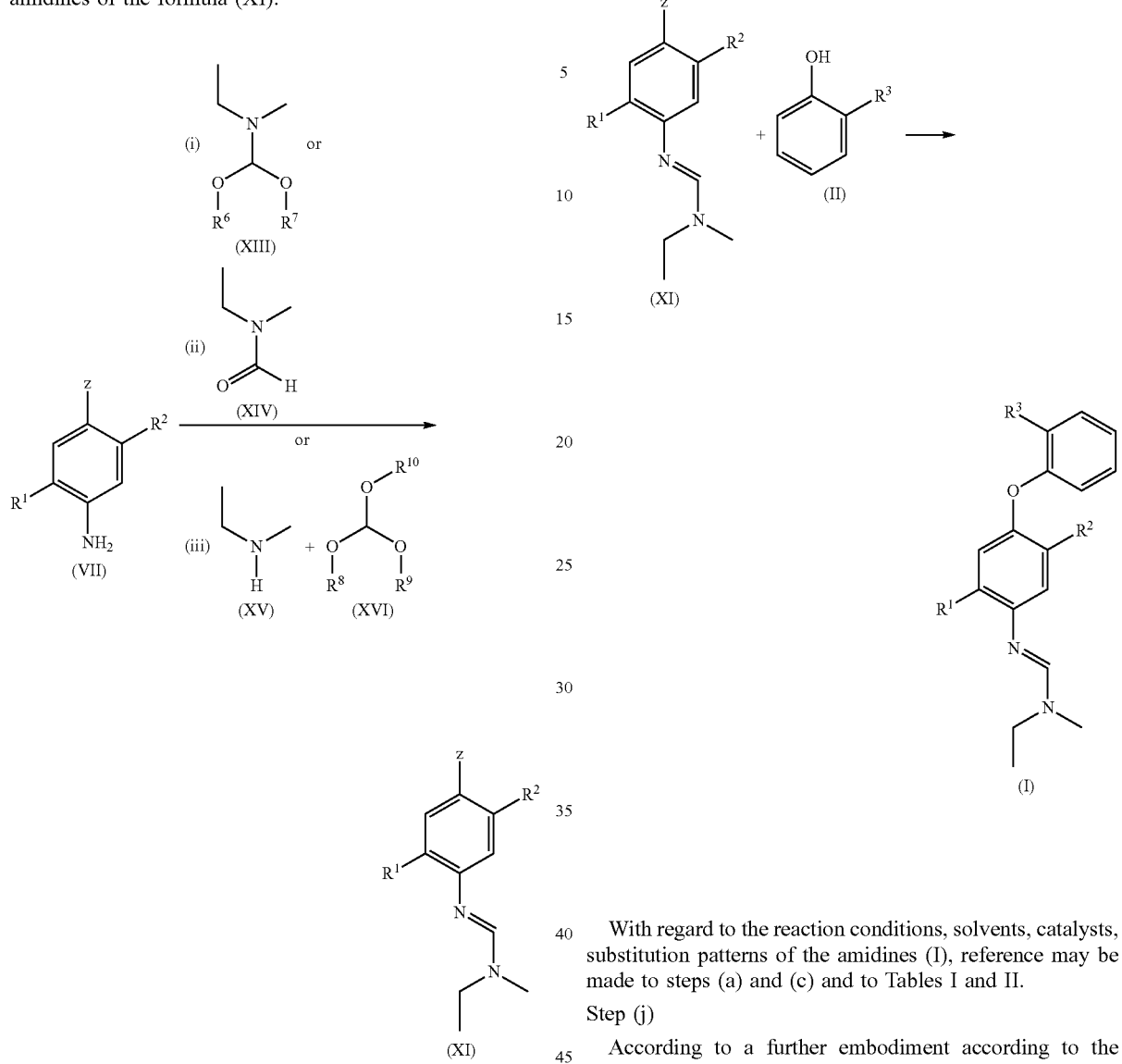

With regard to the reaction conditions, solvents, catalysts and substitution patterns of the amidines (XI), reference may be made to step (f) and to Tables I and II.

The further conversion of the amidines of the formula (XI) into the target molecules of the formula (I) according to the invention can be carried out, for example, as described in step (i).

Step (i)

According to a further embodiment according to the invention, the amidines of the formula (XI) obtainable from step (h) can be reacted with phenol derivatives of the formula (II) or the phenoxides formed therefrom to give the target molecules of the formula (I) according to the invention, in accordance with the reaction scheme below:

With regard to the reaction conditions, solvents, catalysts, substitution patterns of the amidines (I), reference may be made to steps (a) and (c) and to Tables I and II.

Step (j)

According to a further embodiment according to the invention, the amidines of the formula (X) obtainable from step (g) can be reacted with phenyl derivatives of the formula (IV) to give the target molecules of the formula (I) according to the invention, in accordance with the reaction scheme below:

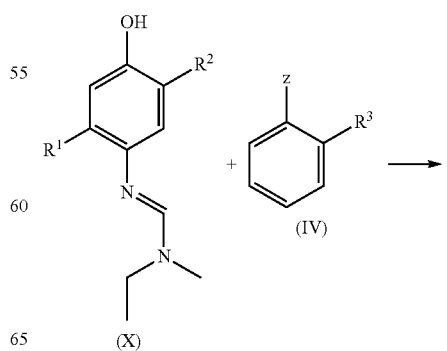

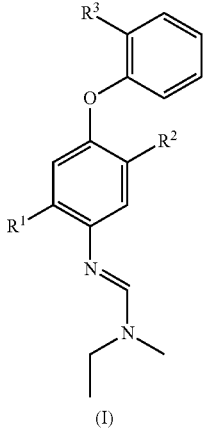

With regard to the reaction conditions, solvents, catalysts and substitution patterns of the amidines (I), reference may be made to steps (a) and (c) and to Tables I and II.

In connection with the processes according to the invention for preparing the amidines of the formula (I), the following combinations of reaction steps are to be regarded as advantageous: steps (a), (e) and (f); steps (b), (e) and (f); steps (c) and (f); steps (d) and (f); steps (h) and (i) and/or steps (g) and (j).

The preparation of the halogen-substituted phenoxyphenylamidines according to the invention is if appropriate carried out without intermediate isolation of the intermediates.

The final purification of the halogen-substituted phenoxyphenylamidines can if appropriate be carried out using customary purification methods. Preferably, purification is carried out by crystallization.

Controlling of Undesirable Microorganisms

The compounds of the formula (I) have potent microbicidal activity and can be used for control of unwanted microorganisms, such as fungi and bacteria, in crop protection, in the protection of materials and in medicinal and in nonmedicinal applications.

Plant Protection

The compounds of the formula (I) have very good fungicidal properties and can be used in crop protection, for example for control of Plasmodiophoromycetes, Oomycetes, Chytridiomycetes, Zygomycetes, Ascomycetes, Basidiomycetes and Deuteromycetes.

Bactericides can be used in crop protection, for example, for control of Pseudomonadaceae, *Xanthomonas*, Rhizobiaceae, Enterobacteriaceae, Corynebacteriaceae and Streptomycetaceae.

The compounds of the formula (I) can be used for curative or protective control of phytopathogenic fungi. The invention therefore also relates to curative and protective methods for controlling phytopathogenic fungi by the use of the inventive active ingredients or compositions, which are applied to the seed, the plant or plant parts, the fruit or the soil in which the plants grow.

Mention may be made, by way of example but without limitation, of some pathogens of fungal and bacterial diseases which come under the generic terms listed above:

diseases caused by powdery mildew pathogens, for example *Blumeria* species, for example *Blumeria graminis*; *Podosphaera* species, for example *Podosphaera leucotricha*; *Sphaerotheca* species, for example *Sphaerotheca fuliginea*; *Uncinula* species, for example *Uncinula necator*;

diseases caused by rust disease pathogens, for example *Gymnosporangium* species, for example *Gymnosporangium sabinae*; *Hemileia* species, for example *Hemileia vastatrix*; *Phakopsora* species, for example *Phakopsora pachyrhizi* or *Phakopsora meibomiae*; *Puccinia* species, for example *Puccinia recondita, Puccinia graminis* oder *Puccinia striiformis*; *Uromyces* species, for example *Uromyces appendiculatus*;

diseases caused by pathogens from the group of the Oomycetes, for example *Albugo* species, for example *Albugo candida*; *Bremia* species, for example *Bremia lactucae*; *Peronospora* species, for example *Peronospora pisi* or *P. brassicae*; *Phytophthora* species, for example *Phytophthora infestans*; *Plasmopara* species, for example *Plasmopara viticola*; *Pseudoperonospora* species, for example *Pseudoperonospora humuli* or *Pseudoperonospora cubensis*; *Pythium* species, for example *Pythium ultimum*;

leaf blotch diseases and leaf wilt diseases caused, for example, by *Alternaria* species, for example *Alternaria solani*; *Cercospora* species, for example *Cercospora beticola*; *Cladiosporium* species, for example *Cladiosporium cucumerinum*; *Cochliobolus* species, for example *Cochliobolus sativus* (conidial form: *Drechslera*, syn: *Helminthosporium*) or *Cochliobolus miyabeanus*; *Colletotrichum* species, for example *Colletotrichum lindemuthanium*; *Cycloconium* species, for example *Cycloconium oleaginum*; *Diaporthe* species, for example *Diaporthe citri*; *Elsinoe* species, for example *Elsinoe fawcettii*; *Gloeosporium* species, for example *Gloeosporium laeticolor*; *Glomerella* species, for example *Glomerella cingulata*; *Guignardia* species, for example *Guignardia bidwelli*; *Leptosphaeria* species, for example *Leptosphaeria maculans*; *Magnaporthe* species, for example *Magnaporthe grisea*; *Microdochium* species, for example *Microdochium nivale*; *Mycosphaerella* species, for example *Mycosphaerella graminicola, Mycosphaerella arachidicola* or *Mycosphaerella fijiensis*; *Phaeosphaeria* species, for example *Phaeosphaeria nodorum*; *Pyrenophora* species, for example *Pyrenophora teres* or *Pyrenophora tritici repentis*; *Ramularia* species, for example *Ramularia collo-cygni* or *Ramularia areola*; *Rhynchosporium* species, for example *Rhynchosporium secalis*; *Septoria* species, for example *Septoria apii* or *Septoria lycopersici*; *Stagonospora* species, for example *Stagonospora nodorum*; *Typhula* species, for example *Typhula incarnata*; *Venturia* species, for example *Venturia inaequalis*;

root and stem diseases caused, for example, by *Corticium* species, for example *Corticium graminearum*; *Fusarium* species, for example *Fusarium oxysporum*; *Gaeumannomyces* species, for example *Gaeumannomyces graminis*; *Plasmodiophora* species, for example *Plasmodiophora brassicae*; *Rhizoctonia* species, for example *Rhizoctonia solani*; *Sarocladium* species, for example *Sarocladium oryzae*; *Sclerotium* species, for example *Sclerotium oryzae*; *Tapesia* species, for example *Tapesia acuformis*; *Thielaviopsis* species, for example *Thielaviopsis basicola*;

ear and panicle diseases (including corn cobs) caused, for example, by *Alternaria* species, for example *Alternaria* spp.; *Aspergillus* species, for example *Aspergillus flavus*; *Cladosporium* species, for example *Cladosporium cladosporioides*; *Claviceps* species, for example *Claviceps purpurea*; *Fusarium* species, for example *Fusarium culmorum*; *Gibberella* species, for example *Gibberella zeae*; *Monographella* species, for example *Monographella nivalis*; *Stagnospora* species, for example *Stagnospora nodorum*;

diseases caused by smut fungi, for example *Sphacelotheca* species, for example *Sphacelotheca reiliana*; *Tilletia* species, for example *Tilletia caries* or *Tilletia controversa*; *Urocystis* species, for example *Urocystis occulta*; *Ustilago* species, for example *Ustilago nuda*;

fruit rot caused, for example, by *Aspergillus* species, for example *Aspergillus flavus*; *Botrytis* species, for example *Botrytis cinerea*; *Penicillium* species, for example *Penicillium expansum* or *Penicillium purpurogenum*; *Rhizopus* species, for example *Rhizopus stolonifer*; *Sclerotinia* species, for example *Sclerotinia sclerotiorum*; *Verticilium* species, for example *Verticilium alboatrum*;

seed-and soil-borne rot and wilt diseases, and also diseases of seedlings, caused, for example, by *Alternaria* species, for example *Alternaria brassicicola*; *Aphanomyces* species, for example *Aphanomyces euteiches*; *Ascochyta* species, for example *Ascochyta lentis*; *Aspergillus* species, for example *Aspergillus flavus*; *Cladosporium* species, for example *Cladosporium herbarum*; *Cochliobolus* species, for example *Cochliobolus sativus* (conidial form: *Drechslera, Bipolaris* Syn: *Helminthosporium*); *Colletotrichum* species, for example *Colletotrichum coccodes*; *Fusarium* species, for example *Fusarium culmorum*; *Gibberella* species, for example *Gibberella zeae*; *Macrophomina* species, for example *Macrophomina phaseolina*; *Microdochium* species, for example *Microdochium nivale*; *Monographella* species, for example *Monographella nivalis*; *Penicillium* species, for example *Penicillium expansum*; *Phoma* species, for example *Phoma lingam*; *Phomopsis* species, for example *Phomopsis sojae*; *Phytophthora* species, for example *Phytophthora cactorum*; *Pyrenophora* species, for example *Pyrenophora graminea*; *Pyricularia* species, for example *Pyricularia oryzae*; *Pythium* species, for example *Pythium ultimum*; *Rhizoctonia* species, for example *Rhizoctonia solani*; *Rhizopus* species, for example *Rhizopus oryzae*; *Sclerotium* species, for example *Sclerotium rolfsii*; *Septoria* species, for example *Septoria nodorum*; *Typhula* species, for example *Typhula incarnata*; *Verticillium* species, for example *Verticillium dahliae*;

cancers, galls and witches' broom caused, for example, by *Nectria* species, for example *Nectria galligena*;

wilt diseases caused, for example, by *Monilinia* species, for example *Monilinia laxa*;

deformations of leaves, flowers and fruits caused, for example, by *Exobasidium* species, for example *Exobasidium vexans*; *Taphrina* species, for example *Taphrina deformans*;

degenerative diseases in woody plants, caused, for example, by *Esca* species, for example *Phaeomoniella chlamydospora, Phaeoacremonium aleophilum* or *Fomitiporia mediterranea*; *Ganoderma* species, for example *Ganoderma boninense*;

diseases of flowers and seeds caused, for example, by *Botrytis* species, for example *Botrytis cinerea*;

diseases of plant tubers caused, for example, by *Rhizoctonia* species, for example *Rhizoctonia solani*; *Helminthosporium* species, for example *Helminthosporium solani*;

diseases caused by bacterial pathogens, for example *Xanthomonas* species, for example *Xanthomonas campestris* pv. *oryzae*; *Pseudomonas* species, for example *Pseudomonas syringae* pv. *lachrymans*; *Erwinia* species, for example *Erwinia amylovora*.

Preference is given to controlling the following diseases of soya beans:

Fungal diseases on leaves, stems, pods and seeds caused, for example, by *Alternaria* leaf spot (*Alternaria* spec. *atrans tenuissima*), Anthracnose (*Colletotrichum gloeosporoides dematium* var. *truncatum*), brown spot (*Septoria glycines*), *cercospora* leaf spot and blight (*Cercospora kikuchii*), *choanephora* leaf blight (*Choanephora infundibulifera trispora* (Syn.)), *dactuliophora* leaf spot (*Dactuliophora glycines*), downy mildew (*Peronospora manshurica*), *drechslera* blight (*Drechslera glycini*), frogeye leaf spot (*Cercospora sojina*), *leptosphaerulina* leaf spot (*Leptosphaerulina trifolii*), *phyllostica* leaf spot (*Phyllosticta sojaecola*), pod and stem blight (*Phomopsis sojae*), powdery mildew (*Microsphaera diffusa*), *pyrenochaeta* leaf spot (*Pyrenochaeta glycines*), *rhizoctonia* aerial, foliage, and web blight (*Rhizoctonia solani*), rust (*Phakopsora pachyrhizi, Phakopsora meibomiae*), scab (*Sphaceloma glycines*), *stemphylium* leaf blight (*Stemphylium botryosum*), target spot (*Corynespora cassiicola*).

Fungal diseases on roots and the stem base caused, for example, by black root rot (*Calonectria crotalariae*), charcoal rot (*Macrophomina phaseolina*), *fusarium* blight or wilt, root rot, and pod and collar rot (*Fusarium oxysporum, Fusarium orthoceras, Fusarium semitectum, Fusarium equiseti*), *mycoleptodiscus* root rot (*Mycoleptodiscus terrestris*), *neocosmospora* (*Neocosmospora vasinfecta*), pod and stem blight (*Diaporthe phaseolorum*), stem canker (*Diaporthe phaseolorum* var. *caulivora*), *phytophthora* rot (*Phytophthora megasperma*), brown stem rot (*Phialophora gregata*), *pythium* rot (*Pythium aphanidermatum, Pythium irregulare, Pythium debaryanum, Pythium myriotylum, Pythium ultimum*), *rhizoctonia* root rot, stem decay, and damping-off (*Rhizoctonia solani*), *sclerotinia* stem decay (*Sclerotinia sclerotiorum*), *sclerotinia* southern blight (*Sclerotinia rolfsii*), *thielaviopsis* root rot (*Thielaviopsis basicola*).

Preferably, the following diseases of soybeans can be combated:

fungal diseases on leaves, stalks, pods and seeds caused by, e.g.,

*alternaria* leaf spot (*Alternaria* spec. *atrans tenuissima*), anthracnose (*Colletotrichum gloeosporoides dematium* var. *truncatum*), brown spot (*Septoria glycines*), *cercospora* leaf spot and blight (*Cercospora kikuchii*), *choanephora* leaf blight (*Choanephora infundibulifera trispora* (Syn.)), *dactuliophora* leaf spot (*Dactuliophora glycines*), downy mildew (*Peronospora manshurica*), *drechslera* blight (*Drechslera glycini*), frogeye leaf spot (*Cercospora sojina*), *leptosphaerulina* leaf spot (*Leptosphaerulina trifolii*), *phyllostica* leaf spot (*Phyllosticta sojaecola*), pod and stem blight (*Phomopsis sojae*), powdery mildew (*Microsphaera diffusa*), *pyrenochaeta* leaf spot (*Pyrenochaeta glycines*), *rhizoctonia* aerial, foliage, and web blight (*Rhizoctonia solani*), rust (*Phakopsora pachyrhizi*), scab (*Sphaceloma glycines*), *stemphylium* leaf blight (*Stemphylium botryosum*), target spot (*Corynespora cassiicola*)

fungal diseases on roots and the stem base caused by, e.g., black root rot (*Calonectria crotalariae*), charcoal rot (*Macrophomina phaseolina*), *fusarium* blight or wilt, root rot, and pod and collar rot (*Fusarium oxysporum, Fusarium orthoceras, Fusarium semitectum, Fusarium equiseti*), *mycoleptodiscus* root rot (*Mycoleptodiscus terrestris*), *neocosmospora* (*Neocosmopspora vasinfecta*), pod and stem blight (*Diaporthe phaseolorum*), stem canker (*Diaporthe phaseolorum* var. *caulivora*), *phytophthora* rot (*Phytophthora megasperma*), brown stem rot (*Phialophora gregata*), *pythium* rot (*Pythium aphanidermatum, Pythium irregulare, Pythium debaryanum, Pythium myriotylum, Pythium ultimum*), *rhizoctonia* root rot, stem decay, and damping-off (*Rhizoctonia solani*), *sclerotinia* stem decay (*Sclerotinia sclerotiorum*), sclerotinia southern blight (*Sclerotinia rolfsii*), thielaviopsis root rot (*Thielaviopsis basicola*).

The compounds of the formula (I) also exhibit a potent strengthening effect in plants. Accordingly, they can be used for mobilizing the defenses of the plant against attack by undesirable microorganisms.

Plant-strengthening (resistance-inducing) substances in the present context are substances capable of stimulating the defense system of plants in such a way that the treated plants, when subsequently inoculated with undesirable microorganisms, develop a high degree of resistance to these microorganisms.

Further, in context with the present invention plant physiology effects comprise the following:

Abiotic stress tolerance, comprising tolerance to high or low temperatures, drought tolerance and recovery after drought stress, water use efficiency (correlating to reduced water consumption), flood tolerance, ozone stress and UV tolerance, tolerance towards chemicals like heavy metals, salts, pesticides etc.

Biotic stress tolerance, comprising increased fungal resistance and increased resistance against nematodes, viruses and bacteria. In context with the present invention, biotic stress tolerance preferably comprises increased fungal resistance and increased resistance against nematodes.

Increased plant vigor, comprising plant health/plant quality and seed vigor, reduced stand failure, improved appearance, increased recovery after periods of stress, improved pigmentation (e.g. chlorophyll content, stay-green effects, etc.) and improved photosynthetic efficiency.

In the present case, undesirable microorganisms are to be understood as meaning phytopathogenic fungi, bacteria and viruses. The substances according to the invention can thus be used to protect plants from attack by the harmful pathogens mentioned for a certain period of time after the treatment. The period of time for which protection is brought about generally ranges from 1 to 10 days, preferably 1 to 7 days, after the treatment of the plants with the active compounds.

The fact that the active compounds are well tolerated by plants in the concentrations necessary for controlling plant diseases makes possible treatment of above ground plant parts, of plant propagation material and seed, and of the soil.

In this connection, the active compounds according to the invention can be used particularly successfully in controlling cereal diseases, such as, e.g., *Puccinia* species, and diseases in viticulture and in the cultivation of fruit and vegetables, such as, e.g., *Botrytis, Venturia* or *Alternaria* species.

The active compounds according to the invention are also suitable for increasing the crop yield. In addition, they are of lower toxicity and are well tolerated by plants.

All plants and plant parts can be treated in accordance with the invention. Plants are understood here to mean all plants and plant populations, such as desired and undesired wild plants or crop plants (including naturally occurring crop plants). Crop plants may be plants which can be obtained by conventional breeding and optimization methods or by biotechnological and genetic engineering methods or combinations of these methods, including the transgenic plants and including the plant cultivars which are protectable and non-protectable by plant breeders' rights. Plant parts are understood to mean all parts and organs of plants above and below the ground, such as shoot, leaf, flower and root, examples of which include leaves, needles, stalks, stems, flowers, fruit bodies, fruits and seeds, and also roots, tubers and rhizomes. The plant parts also include harvested material and vegetative and generative propagation material, for example cuttings, tubers, rhizomes, slips and seeds.

Plants which can be treated in accordance with the invention include the following: cotton, flax, grapevine, fruit, vegetables, such as Rosaceae sp. (for example pome fruits such as apples and pears, but also stone fruits such as apricots, cherries, almonds and peaches, and soft fruits such as strawberries), Ribesioidae sp., Juglandaceae sp., Betulaceae sp., Anacardiaceae sp., Fagaceae sp., Moraceae sp., Oleaceae sp., Actinidaceae sp., Lauraceae sp., Musaceae sp. (for example banana trees and plantations), Rubiaceae sp. (for example coffee), Theaceae sp., Sterculiceae sp., Rutaceae sp. (for example lemons, oranges and grapefruit); Solanaceae sp. (for example tomatoes), Liliaceae sp., Asteraceae sp. (for example lettuce), Umbelliferae sp., Cruciferae sp., Chenopodiaceae sp., Cucurbitaceae sp. (for example cucumber), Alliaceae sp. (for example leek, onion), Papilionaceae sp. (for example peas); major crop plants, such as Gramineae sp. (for example maize, turf, cereals such as wheat, rye, rice, barley, oats, millet and triticale), Asteraceae sp. (for example sunflower), Brassicaceae sp. (for example white cabbage, red cabbage, broccoli, cauliflower, Brussels sprouts, pak choi, kohlrabi, radishes, and oilseed rape, mustard, horseradish and cress), Fabacae sp. (for example bean, peanuts), Papilionaceae sp. (for example soya bean), Solanaceae sp. (for example potatoes), Chenopodiaceae sp. (for example sugar beet, fodder beet, swiss chard, beetroot); useful plants and ornamental plants for gardens and wooded areas; and genetically modified varieties of each of these plants.

Antimycotic Activity

In addition, the inventive compounds of the formula (I) also have very good antimycotic effects. They have a very broad antimycotic activity spectrum, especially against dermatophytes and yeasts, moulds and diphasic fungi, (for example against *Candida* species, such as *Candida albicans, Candida glabrata*), and *Epidermophyton floccosum, Aspergillus* species, such as *Aspergillus niger* and *Aspergillus fumigatus, Trichophyton* species, such as *Trichophyton mentagrophytes, Microsporon* species such as *Microsporon canis* and *M. audouinii*. The list of these fungi by no means constitutes a restriction of the mycotic spectrum covered, and is merely of illustrative character.

The inventive active ingredients of the formula (I) can therefore be used both in medical and in non-medical applications.

Mycotoxins

In addition, the compounds of the formula (I) can reduce the mycotoxin content in the harvested material and the foods and feeds prepared therefrom. Mycotoxins include particularly, but not exclusively, the following: deoxynivalenol (DON), nivalenol, 15-Ac-DON, 3-Ac-DON, T2- and HT2-toxin, fumonisins, zearalenon, moniliformin, fusarin, diaceotoxyscirpenol (DAS), beauvericin, enniatin, fusaroproliferin, fusarenol, ochratoxins, patulin, ergot alkaloids and aflatoxins which can be produced, for example, by the following fungi: *Fusarium* spec., such as *F. acuminatum, F. asiaticum, F. avenaceum, F. crookwellense, F. culmorum, F. graminearum* (*Gibberella zeae*), *F. equiseti, F. fujikoroi, F. musarum, F. oxysporum, F. proliferatum, F. poae, F. pseudograminearum, F. sam-bucinum, F. scirpi, F. semitectum, F. solani, F. sporotrichoides, F. langsethiae, F. subglutinans, F. tricinctum, F. verticillioides* etc., and also by *Aspergillus* spec., such as *A. flavus, A. parasiticus, A. nomius, A. ochraceus, A. clavatus, A. terreus, A. versicolor, Penicillium* spec., such as *P. verrucosum, P. viridicatum, P. citrinum, P. expansum, P. claviforme, P. roqueforti, Claviceps* spec., such as *C. purpurea, C. fusiformis, C. paspali, C. africana, Stachybotrys* spec. and others.

Material Protection

The compounds of the formula (I) can also be used in the protection of materials, for protection of industrial materials against attack and destruction by fungi.

In addition, the compounds of the formula (I) can be used as antifouling compositions, alone or in combinations with other active ingredients.

Industrial materials in the present context are understood to mean inanimate materials which have been prepared for use in industry. For example, industrial materials which are to be protected by inventive compositions from microbial alteration or destruction may be adhesives, glues, paper, wallpaper and board/cardboard, textiles, carpets, leather, wood, fibers and tissues, paints and plastic articles, cooling lubricants and other materials which can be infected with or destroyed by microorganisms. Parts of production plants and buildings, for example cooling-water circuits, cooling and heating systems and ventilation and air-conditioning units, which may be impaired by the proliferation of microorganisms may also be mentioned within the scope of the materials to be protected. Industrial materials within the scope of the present invention preferably include adhesives, sizes, paper and card, leather, wood, paints, cooling lubricants and heat transfer fluids, more preferably wood.

The compounds of the formula (I) may prevent adverse effects, such as rotting, decay, discoloration, decoloration or formation of mould.

In the case of treatment of wood the compounds of the formula (I) may also be used against fungal diseases liable to grow on or inside timber. The term "timber" means all types of species of wood, and all types of working of this wood intended for construction, for example solid wood, high-density wood, laminated wood, and plywood. The method for treating timber according to the invention mainly consists in contacting a composition according to the invention; this includes for example direct application, spraying, dipping, injection or any other suitable means.

In addition, the compounds of the formula (I) can be used to protect objects which come into contact with saltwater or brackish water, especially hulls, screens, nets, buildings, moorings and signalling systems, from fouling.

The compounds of the formula (I) can also be employed for protecting storage goods. Storage goods are understood to mean natural substances of vegetable or animal origin or processed products thereof which are of natural origin, and for which long-term protection is desired. Storage goods of vegetable origin, for example plants or plant parts, such as stems, leaves, tubers, seeds, fruits, grains, can be protected freshly harvested or after processing by (pre)drying, moistening, comminuting, grinding, pressing or roasting. Storage goods also include timber, both unprocessed, such as construction timber, electricity poles and barriers, or in the form of finished products, such as furniture. Storage goods of animal origin are, for example, hides, leather, furs and hairs. The inventive compositions may prevent adverse effects, such as rotting, decay, discoloration, decoloration or formation of mould.

Microorganisms capable of degrading or altering the industrial materials include, for example, bacteria, fungi, yeasts, algae and slime organisms. The compounds of the formula (I) preferably act against fungi, especially moulds, wood-discoloring and wood-destroying fungi (Ascomycetes, Basidiomycetes, Deuteromycetes and Zygomycetes), and against slime organisms and algae. Examples include microorganisms of the following genera: *Alternaria*, such as *Alternaria tenuis*; *Aspergillus*, such as *Aspergillus niger*; *Chaetomium*, such as *Chaetomium globosum*; *Coniophora*, such as *Coniophora puetana*; *Lentinus*, such as *Lentinus tigrinus*; *Penicillium*, such as *Penicillium glaucum*; *Polyporus*, such as *Polyporus versicolor*; *Aureobasidium*, such as *Aureobasidium pullulans*; *Sclerophoma*, such as *Sclerophoma pityophila*; *Trichoderma*, such as *Trichoderma viride*; *Ophiostoma* spp., *Ceratocystis* spp., *Humicola* spp., *Petriella* spp., *Trichurus* spp., *Coriolus* spp., *Gloeophyllum* spp., *Pleurotus* spp., *Poria* spp., *Serpula* spp. and *Tyromyces* spp., *Cladosporium* spp., *Paecilomyces* spp. *Mucor* spp., *Escherichia*, such as *Escherichia coli*; *Pseudomonas*, such as *Pseudomonas aeruginosa*; *Staphylococcus*, such as *Staphylococcus aureus*, *Candida* spp. and *Saccharomyces* spp., such as *Saccharomyces cerevisae*.

Formulations

The present invention further relates to a composition for controlling unwanted microorganisms, comprising at least one of the compounds of the formula (I). These are preferably fungicidal compositions which comprise agriculturally suitable auxiliaries, solvents, carriers, surfactants or extenders. The term "compositions" encompasses agrochemical formulations.

According to the invention, a carrier is a natural or synthetic, organic or inorganic substance with which the active ingredients are mixed or combined for better applicability, in particular for application to plants or plant parts or seed. The carrier, which may be solid or liquid, is generally inert and should be suitable for use in agriculture.

Useful solid carriers include: for example ammonium salts and natural rock flours, such as kaolins, clays, talc, chalk, quartz, attapulgite, montmorillonite or diatomaceous earth, and synthetic rock flours, such as finely divided silica, alumina and silicates; useful solid carriers for granules include: for example, crushed and fractionated natural rocks such as calcite, marble, pumice, sepiolite and dolomite, and also synthetic granules of inorganic and organic flours, and granules of organic material such as paper, sawdust, coconut shells, maize cobs and tobacco stalks; useful emulsifiers and/or foam-formers include: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and also protein hydrolysates; suitable dispersants are nonionic and/or ionic substances, for example from the classes of the alcohol-POE and/or -POP ethers, acid and/or POP POE esters, alkylaryl and/or POP POE ethers, fat and/or POP POE adducts, POE- and/or POP-polyol derivatives, POE- and/or POP-sorbitan or -sugar adducts, alkyl or aryl sulphates, alkyl- or arylsulphonates and alkyl or aryl phosphates or the corresponding PO-ether adducts. Additionally suitable are oligo- or polymers, for example those derived from vinylic monomers, from acrylic acid, from EO and/or PO alone or in combination with, for example, (poly)alcohols or (poly)amines. It is also possible to use lignin and its sulphonic acid derivatives, unmodified and modified celluloses, aromatic and/or aliphatic sulphonic acids and also their adducts with formaldehyde.

The active ingredients can be converted to the customary formulations, such as solutions, emulsions, wettable powders, water- and oil-based suspensions, powders, dusts, pastes, soluble powders, soluble granules, granules for broadcasting, suspoemulsion concentrates, natural products impregnated with active ingredient, synthetic substances impregnated with active ingredient, fertilizers and also microencapsulations in polymeric substances.

The active ingredients can be applied as such, in the form of their formulations or the use forms prepared therefrom, such as ready-to-use solutions, emulsions, water- or oil-based suspensions, powders, wettable powders, pastes, soluble powders, dusts, soluble granules, granules for broadcasting, suspoemulsion concentrates, natural products impregnated with active ingredient, synthetic substances impregnated with active ingredient, fertilizers and also microencapsulations in polymeric substances. Application is accomplished in a customary manner, for example by watering, spraying, atomizing, broadcasting, dusting, foaming, spreading-on and the like. It is also possible to deploy the active ingredients by the ultra-low volume method or to inject the active ingredient preparation/the active ingredient itself into the soil. It is also possible to treat the seed of the plants.

The formulations mentioned can be prepared in a manner known per se, for example by mixing the active ingredients with at least one customary extender, solvent or diluent, emulsifier, dispersant and/or binder or fixing agent, wetting agent, a water repellent, if appropriate siccatives and UV stabilizers and if appropriate dyes and pigments, antifoams, preservatives, secondary thickeners, stickers, gibberellins and also other processing auxiliaries.

The present invention includes not only formulations which are already ready for use and can be deployed with a suitable apparatus to the plant or the seed, but also commercial concentrates which have to be diluted with water prior to use.

The compounds of the formula (I) may be present as such or in their (commercial) formulations and in the use forms prepared from these formulations as a mixture with other (known) active ingredients, such as insecticides, attractants, sterilants, bactericides, acaricides, nematicides, fungicides, growth regulators, herbicides, fertilizers, safeners and/or semiochemicals.

The auxiliaries used may be those substances which are suitable for imparting particular properties to the composition itself or and/or to preparations derived therefrom (for example spray liquors, seed dressings), such as certain technical properties and/or also particular biological properties. Typical auxiliaries include: extenders, solvents and carriers.

Suitable extenders are, for example, water, polar and nonpolar organic chemical liquids, for example from the classes of the aromatic and nonaromatic hydrocarbons (such as paraffins, alkylbenzenes, alkylnaphthalenes, chlorobenzenes), the alcohols and polyols (which may optionally also be substituted, etherified and/or esterified), the ketones (such as acetone, cyclohexanone), esters (including fats and oils) and (poly)ethers, the unsubstituted and substituted amines, amides, lactams (such as N-alkylpyrrolidones) and lactones, the sulphones and sulphoxides (such as dimethyl sulphoxide).

Liquefied gaseous extenders or carriers are understood to mean liquids which are gaseous at standard temperature and under standard pressure, for example aerosol propellants such as halohydrocarbons, or else butane, propane, nitrogen and carbon dioxide.

In the formulations it is possible to use tackifiers such as carboxymethylcellulose, natural and synthetic polymers in the form of powders, granules or latices, such as gum arabic, polyvinyl alcohol and polyvinyl acetate, or else natural phospholipids such as cephalins and lecithins and synthetic phospholipids. Further additives may be mineral and vegetable oils.

If the extender used is water, it is also possible to use, for example, organic solvents as auxiliary solvents. Useful liquid solvents are essentially: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, or else water.

Compositions comprising compounds of the formula (I) may additionally comprise further components, for example surfactants. Suitable surfactants are emulsifiers and/or foam formers, dispersants or wetting agents having ionic or non-ionic properties, or mixtures of these surfactants. Examples thereof are salts of polyacrylic acid, salts of lignosulphonic acid, salts of phenolsulphonic acid or naphthalenesulphonic acid, polycondensates of ethylene oxide with fatty alcohols or with fatty acids or with fatty amines, substituted phenols (preferably alkylphenols or arylphenols), salts of sulphosuccinic esters, taurine derivatives (preferably alkyl taurates), phosphoric esters of polyethoxylated alcohols or phenols, fatty esters of polyols, and derivatives of the compounds containing sulphates, sulphonates and phosphates, for example alkylaryl polyglycol ethers, alkylsulphonates, alkyl sulphates, arylsulphonates, protein hydrolysates, lignosulphite waste liquors and methylcellulose. The presence of a surfactant is necessary if one of the active ingredients and/or one of the inert carriers is insoluble in water and when application is effected in water. The proportion of surfactants is between 5 and 40 percent by weight of the inventive composition.

It is possible to use dyes such as inorganic pigments, for example iron oxide, titanium oxide and Prussian Blue, and organic dyes such as alizarin dyes, azo dyes and metal phthalocyanine dyes, and trace nutrients such as salts of iron, manganese, boron, copper, cobalt, molybdenum and zinc.

Further additives may be perfumes, mineral or vegetable, optionally modified oils, waxes and nutrients (including trace nutrients), such as salts of iron, manganese, boron, copper, cobalt, molybdenum and zinc.

Additional components may be stabilizers, such as cold stabilizers, preservatives, antioxidants, light stabilizers, or other agents which improve chemical and/or physical stability.

If appropriate, other additional components may also be present, for example protective colloids, binders, adhesives, thickeners, thixotropic substances, penetrants, stabilizers, sequestering agents, complex formers. In general, the active ingredients can be combined with any solid or liquid additive commonly used for formulation purposes.

The formulations contain generally between 0.05 and 99% by weight, 0.01 and 98% by weight, preferably between 0.1 and 95% by weight, more preferably between 0.5 and 90% of active ingredient, most preferably between 10 and 70 percent by weight.

The formulations described above can be used for controlling unwanted microorganisms, in which the compositions comprising compounds of the formula (I) are applied to the microorganisms and/or in their habitat.

Seed Treatment

The invention furthermore includes a method for treating seed.

A further aspect of the present invention relates in particular to seeds (dormant, primed, pregerminated or even with emerged roots and leaves) treated with at least one of the compounds of the formula (I). The inventive seeds are used in methods for protection of seeds and emerged plants from the seeds from phytopathogenic harmful fungi. In these methods, seed treated with at least one inventive active ingredient is used.

The compounds of the formula (I) are also suitable for the treatment of seeds and young seedlings. A large part of the damage to crop plants caused by harmful organisms is triggered by the infection of the seeds before sowing or after germination of the plant. This phase is particularly critical since the roots and shoots of the growing plant are particularly sensitive, and even small damage may result in the death of the plant. Accordingly, there is great interest in protecting the seed and the germinating plant by using appropriate compositions.

It is also desirable to optimize the amount of the active ingredient used so as to provide the best possible protection for the seeds, the germinating plants and emerged seedlings from attack by phytopathogenic fungi, but without damaging the plants themselves by the active ingredient used. In particular, methods for the treatment of seed should also take into consideration the intrinsic phenotypes of transgenic plants in order to achieve optimum protection of the seed and the germinating plant with a minimum of crop protection compositions being employed.

The present invention therefore also relates to a method for protecting seeds, germinating plants and emerged seedlings against attack by animal pests and/or phytopathogenic harmful microorganisms by treating the seeds with an inventive composition. The invention also relates to the use of the compositions according to the invention for treating seeds for protecting the seeds, the germinating plants and emerged seedlings against animal pests and/or phytopathogenic microorganisms. The invention further relates to seeds which has been treated with an inventive composition for protection from animal pests and/or phytopathogenic microorganisms.

One of the advantages of the present invention is that the treatment of the seeds with these compositions not only protects the seed itself, but also the resulting plants after emergence, from animal pests and/or phytopathogenic harmful microorganisms. In this way, the immediate treatment of the crop at the time of sowing or shortly thereafter protect plants as well as seed treatment in prior to sowing. It is likewise considered to be advantageous that the inventive active ingredients or compositions can be used especially also for transgenic seed, in which case the plant which grows from this seed is capable of expressing a protein which acts against pests, herbicidal damage or abiotic stress. The treatment of such seeds with the inventive active ingredients or compositions, for example an insecticidal protein, can result in control of certain pests. Surprisingly, a further synergistic effect can be observed in this case, which additionally increases the effectiveness for protection against attack by pests., microorganisms, weeds or abiotic stress.

The compounds of the formula (I) are suitable for protection of seed of any plant variety which is used in agriculture, in the greenhouse, in forests or in horticulture. More particularly, the seed is that of cereals (such as wheat, barley, rye, millet and oats), oilseed rape, maize, cotton, soybean, rice, potatoes, sunflower, beans, coffee, beet (e.g. sugar beet and fodder beet), peanut, vegetables (such as tomato, cucumber, onions and lettuce), lawns and ornamental plants. Of particular significance is the treatment of the seed of wheat, soybean, oilseed rape, maize and rice.

As also described below, the treatment of transgenic seed with the inventive active ingredients or compositions is of particular significance. This refers to the seed of plants containing at least one heterologous gene which allows the expression of a polypeptide or protein, e.g. having insecticidal properties. These heterologous genes in transgenic seeds may originate, for example, from microorganisms of the species *Bacillus, Rhizobium, Pseudomonas, Serratia, Trichoderma, Clavibacter, Glomus* or *Gliocladium*. These heterologous genes preferably originates from *Bacillus* sp., in which case the gene product is effective against the European corn borer and/or the Western corn rootworm. Particularly preferably, the heterologous genes originate from *Bacillus thuringiensis*.

In the context of the present invention, the inventive composition is applied to seeds either alone or in a suitable formulation. Preferably, the seed is treated in a state in which it is sufficiently stable for no damage to occur in the course of treatment. In general, seeds can be treated at any time between harvest and some time after sowing. It is customary to use seed which has been separated from the plant and freed from cobs, shells, stalks, coats, hairs or the flesh of the fruits. For example, it is possible to use seed which has been harvested, cleaned and dried down to a moisture content of less than 15% by weight. Alternatively, it is also possible to use seed which, after drying, for example, has been treated with water and then dried again, or seeds just after priming, or seeds stored in primed conditions or pregerminated seeds, or seeds sown on nursery trays, tapes or paper.

When treating the seeds, it generally has to be ensured that the amount of the inventive composition applied to the seed and/or the amount of further additives is selected such that the germination of the seed is not impaired, or that the resulting plant is not damaged. This must be ensured particularly in the case of active ingredients which can exhibit phytotoxic effects at certain application rates.

The compounds of the formula (I) can be applied directly, i.e. without containing any other components and without having been diluted. In general, it is preferable to apply the compositions to the seed in the form of a suitable formulation. Suitable formulations and methods for seed treatment are known to those skilled in the art. The compounds of the formula (I) can be converted to the customary formulations relevant to on-seed applications, such as solutions, emulsions, suspensions, powders, foams, slurries or combined with other coating compositions for seed, such as film forming materials, pelleting materials, fine iron or other metal powders, granules, coating material for inactivated seeds, and also ULV formulations.

These formulations are prepared in a known manner, by mixing the active ingredients or active ingredient combinations with customary additives, for example customary extenders and solvents or diluents, dyes, wetting agents, dispersants, emulsifiers, antifoams, preservatives, secondary thickeners, adhesives, gibberellins, and also water.

Useful dyes which may be present in the seed dressing formulations usable in accordance with the invention are all dyes which are customary for such purposes. It is possible to use either pigments, which are sparingly soluble in water, or dyes, which are soluble in water. Examples include the dyes known by the names Rhodamine B, C.I. Pigment Red 112 and C.I. Solvent Red 1.

Useful wetting agents which may be present in the seed dressing formulations usable in accordance with the invention are all substances which promote wetting and which are conventionally used for the formulation of active agrochemical ingredients. Usable with preference are alkylnaphthalenesulphonates, such as diisopropyl- or diisobutylnaphthalenesulphonates.

Useful dispersants and/or emulsifiers which may be present in the seed dressing formulations usable in accordance with the invention are all nonionic, anionic and cationic dispersants conventionally used for the formulation of active agrochemical ingredients. Usable with preference are nonionic or anionic dispersants or mixtures of nonionic or anionic dispersants. Useful nonionic dispersants include especially ethylene oxide/propylene oxide block polymers, alkylphenol polyglycol ethers and tristryrylphenol polyglycol ether, and the phosphated or sulphated derivatives thereof. Suitable anionic dispersants are especially lignosulphonates, polyacrylic acid salts and arylsulphonate/formaldehyde condensates.

Antifoams which may be present in the seed dressing formulations usable in accordance with the invention are all foam-inhibiting substances conventionally used for the formulation of active agrochemical ingredients. Silicone antifoams and magnesium stearate can be used with preference.

Preservatives which may be present in the seed dressing formulations usable in accordance with the invention are all substances usable for such purposes in agrochemical compositions. Examples include dichlorophene and benzyl alcohol hemiformal.

Secondary thickeners which may be present in the seed dressing formulations usable in accordance with the invention are all substances usable for such purposes in agrochemical compositions. Preferred examples include cellulose derivatives, acrylic acid derivatives, xanthan, modified clays and finely divided silica.

Adhesives which may be present in the seed dressing formulations usable in accordance with the invention are all customary binders usable in seed dressing products. Preferred examples include polyvinylpyrrolidone, polyvinyl acetate, polyvinyl alcohol and tylose.

The formulations for on-seed applications usable in accordance with the invention can be used to treat a wide variety of different kinds of seed either directly or after prior dilution with water. For instance, the concentrates or the preparations obtainable therefrom by dilution with water can be used to dress the seed of cereals, such as wheat, barley, rye, oats, and triticale, and also seeds of maize, soybean, rice, oilseed rape, peas, beans, cotton, sunflowers, and beets, or else a wide variety of different vegetable seeds. The formulations usable in accordance with the invention, or the dilute preparations thereof, can also be used for seeds of transgenic plants. In this case, additional synergistic effects may also occur in interaction with the substances formed by expression.

For treatment of seeds with the formulations usable in accordance with the invention, or the preparations prepared therefrom by adding water, all mixing units usable customarily for on-seed applications are useful. Specifically, the procedure in on-seed applications is to place the seeds into a mixer, to add the particular desired amount of the formulations, either as such or after prior dilution with water, and to mix everything until all applied formulations are distributed homogeneously on the seeds. If appropriate, this is followed by a drying operation.

The application rate of the formulations usable in accordance with the invention can be varied within a relatively wide range. It is guided by the particular content of the active ingredients in the formulations and by the seeds. The application rates of each single active ingredient is generally between 0.001 and 15 g per kilogram of seed, preferably between 0.01 and 5 g per kilogram of seed.

GMOs

As already mentioned above, it is possible to treat all plants and their parts in accordance with the invention. In a preferred embodiment, wild plant species and plant cultivars, or those obtained by conventional biological breeding methods, such as crossing or protoplast fusion, and also parts thereof, are treated. In a further preferred embodiment, transgenic plants and plant cultivars obtained by genetic engineering methods, if appropriate in combination with conventional methods (Genetically Modified Organisms), and parts thereof are treated. The terms "parts" or "parts of plants" or "plant parts" have been explained above. More preferably, plants of the plant cultivars which are commercially available or are in use are treated in accordance with the invention. Plant cultivars are understood to mean plants which have new properties ("traits") and have been obtained by conventional breeding, by mutagenesis or by recombinant DNA techniques. They can be cultivars, varieties, bio- or genotypes.

The method of treatment according to the invention can be used in the treatment of genetically modified organisms (GMOs), e.g. plants or seeds. Genetically modified plants (or transgenic plants) are plants of which a heterologous gene has been stably integrated into genome. The expression "heterologous gene" essentially means a gene which is provided or assembled outside the plant and when introduced in the nuclear, chloroplastic or mitochondrial genome gives the transformed plant new or improved agronomic or other properties by expressing a protein or polypeptide of interest or by downregulating or silencing other gene(s) which are present in the plant (using for example, antisense technology, cosuppression technology, RNA interference—RNAi—technology or microRNA—miRNA—technology). A heterologous gene that is located in the genome is also called a transgene. A transgene that is defined by its particular location in the plant genome is called a transformation or transgenic event.

Plants and plant cultivars which are preferably to be treated according to the invention include all plants which have genetic material which impart particularly advantageous, useful traits to these plants (whether obtained by breeding and/or biotechnological means).

Plants and plant cultivars which are also preferably to be treated according to the invention are resistant against one or more biotic stresses, i.e. said plants show a better defense against animal and microbial pests, such as against nematodes, insects, mites, phytopathogenic fungi, bacteria, viruses and/or viroids.

Plants and plant cultivars which may also be treated according to the invention are those plants which are resistant to one or more abiotic stresses. Abiotic stress conditions may include, for example, drought, cold temperature exposure, heat exposure, osmotic stress, flooding, increased soil salinity, increased mineral exposure, ozone exposure, high light exposure, limited availability of nitrogen nutrients, limited availability of phosphorus nutrients, shade avoidance.

Plants and plant cultivars which may also be treated according to the invention, are those plants characterized by enhanced yield characteristics. Increased yield in said plants can be the result of, for example, improved plant physiology, growth and development, such as water use efficiency, water retention efficiency, improved nitrogen use, enhanced carbon assimilation, improved photosynthesis, increased germination efficiency and accelerated maturation. Yield can furthermore be affected by improved plant architecture (under stress and non-stress conditions), including but not limited to, early flowering, flowering control for hybrid seed production, seedling vigor, plant size, internode number and distance, root growth, seed size, fruit size, pod size, pod or ear number, seed number per pod or ear, seed mass, enhanced seed filling, reduced seed dispersal, reduced pod dehiscence and lodging resistance. Further yield traits include seed composition, such as carbohydrate content and composition for example cotton or starch, protein content, oil content and composition, nutritional value, reduction in anti-nutritional compounds, improved processability and better storage stability.

Plants that may be treated according to the invention are hybrid plants that already express the characteristic of heterosis or hybrid vigor which results in generally higher yield, vigor, health and resistance towards biotic and abiotic stresses).

Plants or plant cultivars (obtained by plant biotechnology methods such as genetic engineering) which may be treated according to the invention are herbicide-tolerant plants, i.e. plants made tolerant to one or more given herbicides. Such plants can be obtained either by genetic transformation, or by selection of plants containing a mutation imparting such herbicide tolerance.

Plants or plant cultivars (obtained by plant biotechnology methods such as genetic engineering) which may also be treated according to the invention are insect-resistant transgenic plants, i.e. plants made resistant to attack by certain target insects. Such plants can be obtained by genetic transformation, or by selection of plants containing a mutation imparting such insect resistance.

Plants or plant cultivars (obtained by plant biotechnology methods such as genetic engineering) which may also be treated according to the invention are tolerant to abiotic stresses. Such plants can be obtained by genetic transformation, or by selection of plants containing a mutation imparting such stress resistance.

Plants or plant cultivars (obtained by plant biotechnology methods such as genetic engineering) which may also be treated according to the invention show altered quantity, quality and/or storage-stability of the harvested product and/or altered properties of specific ingredients of the harvested product.

Plants or plant cultivars (that can be obtained by plant biotechnology methods such as genetic engineering) which may also be treated according to the invention are plants, such as cotton plants, with altered fiber characteristics. Such plants can be obtained by genetic transformation, or by selection of plants contain a mutation imparting such altered fiber characteristics.

Plants or plant cultivars (that can be obtained by plant biotechnology methods such as genetic engineering) which may also be treated according to the invention are plants, such as oilseed rape or related *Brassica* plants, with altered oil profile characteristics. Such plants can be obtained by genetic transformation, or by selection of plants contain a mutation imparting such altered oil profile characteristics.

Plants or plant cultivars (that can be obtained by plant biotechnology methods such as genetic engineering) which may also be treated according to the invention are plants, such as oilseed rape or related *Brassica* plants, with altered seed shattering characteristics. Such plants can be obtained by genetic transformation, or by selection of plants contain a mutation imparting such altered seed shattering characteristics and include plants such as oilseed rape plants with delayed or reduced seed shattering.

Plants or plant cultivars (that can be obtained by plant biotechnology methods such as genetic engineering) which may also be treated according to the invention are plants, such as Tobacco plants, with altered post-translational protein modification patterns.

Application Rates

When using the compounds of the formula (I) as fungicides, the application rates can be varied within a relatively wide range, depending on the kind of application. The application rate of the inventive active ingredients is in the case of treatment of plant parts, for example leaves: from 0.1 to 10 000 g/ha, preferably from 10 to 1000 g/ha, more preferably from 20 to 200 g/ha (in the case of application by watering or dripping, it is even possible to reduce the application rate, especially when inert substrates such as rockwool or perlite are used);

in the case of seed treatment: from 0.1 to 200 g per 100 kg of seed, preferably from 1 to 150 g per 100 kg of seed, more preferably from 2.5 to 25 g per 100 kg of seed, even more preferably from 2.5 to 12.5 g per 100 kg of seed;

in the case of soil treatment: from 0.1 to 10 000 g/ha, preferably from 1 to 5000 g/ha.

These application rates are merely by way of example and are not limiting for the purposes of the invention.

The plants listed can be treated according to the invention in a particularly advantageous manner with the compounds of the general formula (I) and/or the active compound mixtures according to the invention. The preferred ranges stated above for the active compounds or mixtures also apply to the treatment of these plants. Particular emphasis is given to the treatment of plants with the compounds or mixtures specifically mentioned in the present text.

The preparation and the use of the active compounds according to the invention is intended to be more fully explained from the following examples without, however, being limited to these.

PREPARATION EXAMPLES

The preparation and the use of the inventive active ingredients of the formula (I) is illustrated by the examples which follow. However, the invention is not limited to these examples.

General Notes: Unless stated otherwise, all chromatographic purification and separation steps are carried out on silica gel and using a solvent gradient from 0:100 ethyl acetate/cyclohexane to 100:0 ethyl acetate/cyclohexane.

Preparation of Compounds of the Formula (I-03)

Step 1

1-chloro-2-(2-chlorophenoxy)-4-methyl-5-nitrobenzene (VI-03)

1.00 g (4.85 mmol) 1,2-dichloro-4-methyl-5-nitrobenzene, 624 mg (2.43 mmol) 2-chlorophenol and 1.34 g (9.71 mmol) potassium carbonate were suspended in 40 ml of dry DMF and heated to 90° C. for 12 h. The mixture was cooled to room temperature mixed with 100 ml water, neutralized with diluted hydrochloric acid and extracted 3 times with ethyl acetate. The organic phase was washed with water, dried over sodium sulfate and concentrated under reduced pressure. Purification of the crude followed by chromatography via Combflash (40 g silica gel, gradient cyclohexane/ethyl acetate) to yield 1.03 g 1-chloro-2-(2-chlorophenoxy)-4-methyl-5-nitrobenzene.

Step 2

5-chloro-4-(2-chlorophenoxy)-2-methylaniline (VIII-03)

1.00 g (3.35 mmol) 1-(2-chlorophenoxy)-2-chloro-5-methyl-4-nitrobenzene was dissolved in 20 ml EtOH followed by addition of 3.78 g (16.8 mmol) tin-dichloride dihydrat (SnCl2*2 H2O) at room temperature. The mixture was refluxed for 1 h, cooled to room temperature, followed by addition of water and adjustment of the pH to 7 by slow addition of sodium carbonate. The water phase was extracted with ethyl acetate, the organic phase dried over MgSO4, then concentrated in vacuum and the crude product chromatographed by chromatography via Combiflash (40 g silica gel, gradient cyclohexane/ethyl acetate) yielding 0.60 g 5-chloro-4-(2-chlorophenoxy)-2-methylaniline.

Step 3

N'-[5-chloro-4-(2-chlorophenoxy)-2-methylphenyl]-N-ethyl-N-methylimidoformamide (I-03)

0.50 g (1.87 mmol) 5-chloro-4-(2-chlorophenoxy)-2-methylaniline and 0.37 g (2.80 mmol) N-(dimethoxymethyl)-N-methylethanamine were dissolved in 13 ml of dry toluene and heated for 6 h at 80° C. The mixture was cooled to room temperature, concentrated under reduced pressure and purified by chromatography via Combiflash (12 g silica gel, solvent: gradient cyclohexane/ethyl acetate) yielding 0.56 g N'-[5-chloro-4-(2-chlorophenoxy)-2-methylphenyl]-N-ethyl-N-methy limidoformamide.

Preparation of Compounds of the Formula (I-03)

Step 1

1-chloro-2-(2-chlorophenoxy)-4-methyl-5-nitrobenzene (VI-03)

1.00 g (4.85 mmol) 1,2-dichloro-4-methyl-5-nitrobenzene, 624 mg (2.43 mmol) 2-chlorophenol and 1.34 g (9.71 mmol) potassium carbonate were suspended in 40 ml of dry DMF and heated to 90° C. for 12 h. The mixture was cooled to room temperature, mixed with water, neutralized with diluted hydrochloric acid and extracted 3 times with ethyl acetate. The organic phase was washed with water, dried over sodium sulfate and concentrated under reduced pressure. Purification of the crude followed by chromatography via Combflash (40 g silica gel, gradient cyclohexane/ethyl acetate) to yield 1.03 g 1-chloro-2-(2-chlorophenoxy)-4-methyl-5-nitrobenzene.

Step 2

5-chloro-4-(2-chlorophenoxy)-2-methylaniline (VIII-03)

1.00 g (3.35 mmol) 1-(2-chlorophenoxy)-2-chloro-5-methyl-4-nitrobenzene was dissolved in 20 ml EtOH followed by addition of 3.78 g (16.8 mmol) tin-dichloride dihydrat (SnCl2*2 H2O) at room temperature. The mixture was refluxed for 1 h, cooled to room temperature, followed by addition of water and adjustment of the pH to 7 by slow addition of sodium carbonate. The water phase was extracted with ethyl acetate, the organic phase dried over MgSO4, then concentrated in vacuum and the crude product chromatographed by chromatography via Combiflash (40 g silica gel, gradient cyclohexane/ethyl acetate) yielding 0.60 g 5-chloro-4-(2-chlorophenoxy)-2-methylaniline.

Step 3

N'-[5-chloro-4-(2-chlorophenoxy)-2-methylphenyl]-N-ethyl-N-methylimidoformamide (I-03)

0.50 g (1.87 mmol) 5-chloro-4-(2-chlorophenoxy)-2-methylaniline and 0.37 g (2.80 mmol) N-(dimethoxymethyl)-N-methylethanamine were dissolved in 13 ml of dry toluene and heated for 6 h at 80° C. The mixture was cooled to room temperature, concentrated under reduced pressure and purified by chromatography via Combiflash (12 g silica gel, solvent: gradient cyclohexane/ethyl acetate) yielding 0.56 g N'-[5-chloro-4-(2-chlorophenoxy)-2-methylphenyl]-N-ethyl-N-methy limidoformamide.

Preparation of Compounds of the Formula (I-05)

Step 1

1-(2-bromophenoxy)-5-methyl-4-nitro-2-(trifluoromethyl)benzene (VI-05)

0.92 g (3.85 mmol) 1-chloro-5-methyl-4-nitro-2-(trifluoromethyl)benzene, 0.67 g (3.85 mmol) 2-bromophenol and 1.06 g (7.70 mmol) potassium carbonate were suspended in 30 ml of dry DMF and stirred at room temperature for 16 h. The mixture was mixed with water, neutralized with diluted hydrochloric acid and extracted 3 times with ethyl acetate. The organic phase was washed with water, dried over sodium sulfate and concentrated under reduced pressure. Purification of the crude followed by chromatography via Combflash (40 g silica gel, gradient cyclohexane/ethyl acetate) to yield 0.42 g 1-(2-bromophenoxy)-5-methyl-4-nitro-2-(trifluoromethyl)benzene.

Step 2

4-(2-bromophenoxy)-2-methyl-5-(trifluoromethyl) aniline (VIII-05)

0.38 g (1.01 mmol) 1-(2-bromophenoxy)-5-methyl-4-nitro-2-(trifluoromethyl)benzene was dissolved in 7 ml MeOH followed by addition of 0.42 ml (5.05 mmol) hydrochloric acid (37%) and 0.28 g (5.05 mmol) iron powder and at room temperature. The mixture was refluxed for 2 h, cooled to room temperature, followed by addition of water and adjustment of the pH to 7 by slow addition of sodium hydrogen carbonate. The water phase was extracted with ethyl acetate, the organic phase dried over MgSO4, then concentrated in vacuum and the crude product chromatographed by chromatography via Combiflash (40 g silica gel, gradient cyclohexane/ethyl acetate) yielding 0.60 g 4-(2-bromophenoxy)-2-methyl-5-(trifluoromethyl)aniline.

Step 3

N'-[4-(2-bromophenoxy)-2-methyl-5-(trifluoromethyl)phenyl]-N-ethyl-N-methylimidoformamide (I-05)

0.13 g (0.38 mmol) 4-(2-bromophenoxy)-2-methyl-5-(trifluoromethyl)aniline and 75 mg (0.56 mmol) N-(dimethoxymethyl)-N-methylethanamine were dissolved in 10 ml of dry toluene and heated for 6 h at 80° C. The mixture was cooled to room temperature, concentrated under reduced pressure and purified by chromatography via Combiflash (12 g silica gel, solvent: gradient cyclohexane/ethyl acetate) yielding 77 mg N'-[4-(2-bromophenoxy)-2-methyl-5-(trifluoromethyl)phenyl]-N-ethyl-N-methylimidoformamide.

EXAMPLES

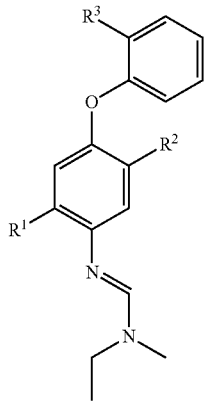

(I)

| Ex N° | $R^1$ | $R^2$ | $R^3$ | LogP |
|---|---|---|---|---|
| I-01 | Me | Cl | F | 1.64[a]; 4.56[b] |
| I-02 | Me | Cl | Br | 1.86[a]; 5.13[b] |
| I-03 | Me | Cl | Cl | 1.55[a] |
| I-04 | Me | $CF_3$ | F | 1.72[a] |
| I-05 | Me | $CF_3$ | Br | 1.90[a] |
| I-06 | Me | Cl | I | 1.81[a] |

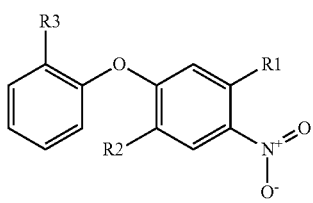

(VI)

| Ex N° | $R^1$ | $R^2$ | $R^3$ | LogP |
|---|---|---|---|---|
| VI-01 | Me | Cl | F | 4.12[a] |
| VI-02 | Me | Cl | Br | |
| VI-03 | Me | Cl | Cl | 4.51[a] |
| VI-04 | Me | $CF_3$ | F | 4.23[a] |
| VI-05 | Me | $CF_3$ | Br | 4.64[a] |
| VI-06 | Me | Cl | I | 4.68[a] |

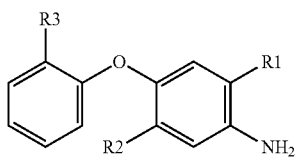

(VIII)

| Ex N° | $R^1$ | $R^2$ | $R^3$ | LogP |
|---|---|---|---|---|
| VIII-01 | Me | Cl | F | 3.00[a]; 3.00[b] |
| VIII-02 | Me | Cl | Br | 3.55[a]; 3.54[b] |
| VIII-03 | Me | Cl | Cl | 3.37[a] |
| VIII-04 | Me | $CF_3$ | F | 3.21[a] |
| VIII-05 | Me | $CF_3$ | Br | 3.68[a] |
| VIII-06 | Me | Cl | I | 3.72[a] |

Measurement of Log P values was performed according to EEC directive 79/831 Annex V.A8 by HPLC (High Performance Liquid Chromatography) on reversed phase columns with the following methods:

[a] Log P value is determined by measurement of LC-UV, in an acidic range, with 0.1% formic acid in water and acetonitrile as eluent (linear gradient from 10% acetonitrile to 95% acetonitrile).

[b] Log P value is determined by measurement of LC-UV, in a neutral range, with 0.001 molar ammonium acetate solution in water and acetonitrile as eluent (linear gradient from 10% acetonitrile to 95% acetonitrile).

Calibration was done with straight-chain alkan2-ones (with 3 to 16 carbon atoms) with known Log P values (measurement of Log P values using retention times with linear interpolation between successive alkanones). Lambda-max-values were determined using UV-spectra from 200 nm to 400 nm and the peak values of the chromatographic signals.

NMR-Peak Lists

1H-NMR data of selected examples are written in form of 1H-NMR-peak lists. To each signal peak are listed the δ-value in ppm and the signal intensity in round brackets. Between the δ-value-signal intensity pairs are semicolons as delimiters.

The peak list of an example has therefore the form:

$\delta_1$ (intensity$_1$); $\delta_2$ (intensity$_2$); ...; $\delta_i$ (intensity$_i$); ...; $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for 1H spectra, we use tetramethylsilane and/or the chemical shift of the solvent used, especially in the case of spectra measured in DMSO. Therefore in NMR peak lists, tetramethylsilane peak can occur but not necessarily.

The 1H-NMR peak lists are similar to classical 1H-NMR prints and contains therefore usually all peaks, which are listed at classical NMR-interpretation.

Additionally they can show like classical 1H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our 1H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical 1H-NMR interpretation.

Further details of NMR-data description with peak lists you find in the publication "Citation of NMR Peaklist Data within Patent Applications" of the Research Disclosure Database Number 564025.

Example I-01: $^1$H-NMR (400.0 MHz, $d_6$-DMSO):

δ = 7.774 (1.2); 7.665 (0.5); 7.374 (1.1); 7.368 (0.7); 7.362 (1.0); 7.357 (0.8); 7.350 (1.4); 7.345 (1.3); 7.340 (1.0); 7.327 (1.2); 7.321 (1.4); 7.148 (0.4); 7.143 (0.6); 7.129 (2.6); 7.124 (2.3); 7.116 (3.1); 7.111 (2.8); 7.105 (2.9); 7.099 (1.4); 7.093 (1.1); 7.079 (0.4); 7.021 (1.5); 7.000 (0.7); 6.909 (6.4); 6.821 (1.2); 6.814 (0.7); 6.809 (1.0); 6.799 (1.6); 6.797 (1.6); 6.782 (0.8); 6.775 (1.0); 3.434 (0.6); 3.361 (1.2); 3.344 (1.3); 3.324 (38.0); 2.996 (1.5); 2.922 (3.8); 2.671 (0.5); 2.667 (0.4); 2.524 (1.4); 2.506 (55.2); 2.502 (72.8); 2.498 (54.7); 2.333 (0.3); 2.329 (0.5); 2.324 (0.4); 2.130 (16.0); 1.154 (1.9); 1.137 (3.9); 1.122 (2.6); 0.000 (3.3)

Example I-02: $^1$H-NMR (400.0 MHz, $d_6$-DMSO):

δ = 7.780 (1.2); 7.700 (2.7); 7.696 (2.8); 7.680 (3.1); 7.676 (3.1); 7.324 (1.3); 7.320 (1.3); 7.303 (2.6); 7.285 (1.6); 7.281 (1.5); 7.046 (1.8); 7.043 (2.1); 7.027 (3.9); 7.024 (3.7); 7.008 (2.0); 7.005 (1.9); 6.910 (6.3); 6.768 (0.4); 6.676 (2.7); 6.673 (2.7); 6.655 (2.6); 6.652 (2.5); 3.436 (0.6); 3.365 (1.2); 3.349 (1.2); 3.330 (0.7); 3.314 (26.2); 2.999 (1.5); 2.964 (0.6); 2.928 (3.7); 2.675 (0.5); 2.670 (0.7); 2.666 (0.5); 2.506 (73.2); 2.501 (96.3); 2.497 (73.0); 2.328 (0.6); 2.324 (0.5); 2.141 (16.0); 2.027 (0.7); 1.157 (2.2); 1.140 (4.3); 1.124 (2.7); 0.146 (0.5); 0.008 (4.3); 0.000 (94.9); −0.008 (5.2); −0.024 (0.4); −0.149 (0.5)

Example I-03: $^1$H-NMR (400.0 MHz, $d_6$-DMSO):

δ = 7.781 (1.2); 7.673 (0.5); 7.557 (2.5); 7.553 (2.7); 7.537 (2.8); 7.533 (2.9); 7.287 (1.2); 7.283 (1.3); 7.264 (2.4); 7.247 (1.6); 7.244 (1.6); 7.115 (1.7); 7.111 (1.8); 7.095 (2.6); 7.092 (2.7); 7.076 (1.3); 7.073 (1.3); 7.033 (1.7); 6.915 (6.5); 6.712 (2.7); 6.709 (2.9); 6.691 (2.6); 6.688 (2.7); 3.760 (0.3); 3.437 (0.7); 3.365 (1.3); 3.348 (1.2); 3.324 (11.8); 3.000 (1.6); 2.929 (4.0); 2.508 (12.6); 2.504 (16.2); 2.499 (12.2); 2.142 (16.0); 1.397 (2.2); 1.156 (2.3); 1.140 (4.5); 1.124 (2.8); 0.000 (3.6)

Example I-04: $^1$H-NMR (400.0 MHz, $d_6$-DMSO):

δ = 7.795 (1.7); 7.681 (0.8); 7.397 (1.3); 7.385 (1.4); 7.380 (1.2); 7.372 (2.1); 7.369 (2.0); 7.362 (1.4); 7.356 (1.8); 7.352 (1.3); 7.344 (2.0); 7.336 (0.6); 7.209 (0.5); 7.206 (0.6); 7.198 (3.2); 7.192 (3.7); 7.187 (4.0); 7.181 (5.5); 7.174 (5.1); 7.129 (2.5); 7.028 (1.6); 7.020 (1.1); 7.015 (1.6); 7.011 (1.4); 7.006 (2.3); 7.004 (2.2); 6.995 (2.0); 6.989 (1.4); 6.982 (1.7); 6.813 (6.7); 3.435 (1.1); 3.371 (1.9); 3.355 (2.0); 3.321 (13.6); 3.002 (2.3); 2.928 (5.6); 2.508 (24.0); 2.503 (32.9); 2.499 (27.0); 2.167 (16.0); 1.139 (6.1); 1.125 (4.9); 0.000 (2.6)

Example I-05: $^1$H-NMR (400.0 MHz, $d_6$-DMSO):

δ = 7.803 (1.8); 7.730 (3.1); 7.727 (3.6); 7.710 (3.5); 7.707 (3.9); 7.691 (0.8); 7.381 (1.5); 7.377 (1.7); 7.359 (3.3); 7.342 (1.9); 7.338 (2.0); 7.147 (2.4); 7.115 (2.3); 7.112 (2.5); 7.093 (3.6); 7.076 (1.6); 7.073 (1.7); 6.869 (3.7); 6.851 (3.2); 6.849 (3.4); 6.786 (6.8); 3.441 (1.0); 3.375 (1.8); 3.359 (1.7); 3.321 (13.4); 3.008 (2.4); 2.932 (5.7); 2.507 (25.2); 2.503 (32.4); 2.499 (26.3); 2.174 (16.0); 1.142 (6.0); 0.000 (2.3)

Example I-06: $^1$H-NMR (400.0 MHz, $d_6$-DMSO):

δ = 7.883 (2.6); 7.879 (2.9); 7.863 (2.8); 7.860 (2.9); 7.778 (1.3); 7.669 (0.5); 7.330 (1.3); 7.326 (1.4); 7.308 (2.6); 7.291 (1.5); 7.287 (1.5); 7.028 (1.7); 6.883 (6.9); 6.873 (3.2); 6.870 (3.1); 6.854 (1.5); 6.851 (1.5); 6.593 (2.9); 6.590 (3.0); 6.572 (2.8); 6.570 (2.8); 5.754 (0.7); 3.437 (0.7); 3.365 (1.4); 3.349 (1.3); 3.318 (16.9); 2.999 (1.6); 2.928 (4.2); 2.506 (31.1); 2.502 (39.5); 2.498 (31.1); 2.139 (16.0); 2.074 (0.6); 1.233 (0.5); 1.155 (2.6); 1.139 (4.9); 1.124 (3.0); 0.000 (1.6)

Example VI-02: $^1$H-NMR (400.0 MHz, $d_6$-DMSO):

δ = 10.176 (3.5); 8.325 (5.4); 7.826 (1.9); 7.810 (1.6); 7.807 (2.1); 7.522 (0.9); 7.518 (0.9); 7.503 (1.8); 7.499 (2.0); 7.483 (1.3); 7.479 (1.3); 7.471 (1.1); 7.467 (1.2); 7.451 (1.2); 7.447 (1.2); 7.308 (1.0); 7.304 (1.5); 7.285 (1.4); 7.265 (3.4); 7.193 (0.6); 7.189 (0.6); 7.173 (1.1); 7.155 (0.8); 7.151 (0.8); 6.958 (1.4); 6.955 (1.5); 6.938 (1.2); 6.934 (1.2); 6.833 (4.8); 6.746 (0.7); 6.743 (0.7); 6.727 (1.2); 6.724 (1.2); 6.708 (0.6); 6.705 (0.6); 3.320 (102.5); 2.671 (0.6); 2.666 (0.5); 2.524 (1.6); 2.506 (66.9); 2.502 (88.3); 2.497 (66.9); 2.438 (16.0); 2.333 (0.4); 2.329 (0.6); 2.324 (0.4); 0.000 (4.6)

Example VI-03: $^1$H-NMR (400.0 MHz, $d_6$-DMSO):

δ = 8.322 (5.4); 7.688 (2.1); 7.668 (2.4); 7.483 (0.9); 7.464 (2.2); 7.447 (1.4); 7.444 (1.5); 7.378 (1.6); 7.359 (2.3); 7.340 (1.0); 7.306 (2.5); 7.286 (2.0); 6.860 (5.1); 3.321 (6.1); 2.505 (16.6); 2.441 (16.0); 2.298 (1.1)

Example VI-04: $^1$H-NMR (400.0 MHz, $d_6$-DMSO):

δ = 8.400 (16.0); 7.520 (2.7); 7.499 (4.5); 7.493 (4.0); 7.481 (1.0); 7.472 (3.9); 7.468 (3.3); 7.437 (4.7); 7.418 (10.9); 7.409 (2.8); 7.404 (5.5); 7.400 (7.8); 7.387 (2.9); 7.362 (5.3); 7.359

(5.4); 7.340 (5.9); 7.323 (2.0); 7.003 (12.9); 3.319 (16.7); 2.893 (1.2); 2.734 (1.0); 2.678 (0.5); 2.673 (0.5); 2.519 (48.1); 2.512 (34.8); 2.508 (57.3); 2.504 (72.1); 2.500 (54.7); 2.331 (0.5); 0.000 (1.6)

Example VI-05: $^1$H-NMR (400.0 MHz, $d_6$-DMSO):

δ = 10.176 (11.1); 8.413 (16.0); 7.953 (2.2); 7.857 (6.2); 7.853 (6.9); 7.837 (6.8); 7.833 (7.3); 7.561 (2.8); 7.558 (3.1); 7.539 (6.3); 7.522 (4.4); 7.519 (4.4); 7.471 (4.7); 7.467 (5.1); 7.451 (5.0); 7.447 (5.3); 7.375 (6.4); 7.372 (9.1); 7.354 (9.0); 7.352 (8.1); 7.338 (7.0); 7.319 (3.4); 7.315 (3.1); 7.194 (2.3); 7.190 (2.5); 7.172 (4.6); 7.155 (3.1); 7.151 (3.1); 6.959 (5.5); 6.956 (6.1); 6.939 (4.7); 6.936 (5.0); 6.841 (13.8); 6.746 (2.9); 6.743 (3.0); 6.727 (4.8); 6.724 (4.9); 6.708 (2.6); 6.705 (2.6); 3.321 (61.8); 2.892 (14.9); 2.733 (13.2); 2.672 (1.0); 2.668 (0.9); 2.507 (133.3); 2.503 (133.3); 2.499 (96.0); 2.343 (0.6); 2.330 (0.8); 2.325 (0.7); 0.000 (2.8)

Example VI-06: $^1$H-NMR (400.0 MHz, $d_6$-DMSO):

δ = 8.326 (6.2); 8.306 (0.9); 8.001 (2.1); 7.997 (2.2); 7.981 (2.2); 7.978 (2.2); 7.897 (0.7); 7.525 (1.0); 7.521 (1.1); 7.505 (1.9); 7.503 (1.9); 7.486 (1.3); 7.483 (1.3); 7.210 (2.3); 7.207 (2.5); 7.190 (2.1); 7.186 (2.2); 7.139 (1.3); 7.135 (1.3); 7.120 (2.1); 7.117 (2.1); 7.101 (1.1); 7.097 (1.1); 6.771 (5.0); 3.321 (9.4); 2.512 (6.8); 2.508 (12.7); 2.504 (18.3); 2.499 (12.2); 2.435 (16.0); 2.297 (1.2); 1.397 (0.6); 0.000 (1.4)

Example VIII-01: $^1$H-NMR (400.0 MHz, $d_6$-DMSO):

δ = 7.334 (0.9); 7.329 (0.7); 7.315 (1.0); 7.309 (1.2); 7.305 (1.1); 7.300 (1.0); 7.285 (1.1); 7.281 (1.2); 7.094 (0.5); 7.090 (0.6); 7.075 (1.6); 7.070 (1.6); 7.061 (1.1); 7.057 (2.4); 7.051 (2.3); 7.045 (1.2); 7.042 (1.2); 7.036 (1.0); 7.031 (1.0); 7.026 (1.0); 7.012 (0.4); 7.007 (0.4); 6.843 (4.9); 6.766 (6.9); 6.700 (1.0); 6.694 (0.9); 6.678 (1.5); 6.675 (1.6); 6.659 (0.9); 6.654 (1.0); 5.110 (4.1); 4.057 (0.6); 4.039 (1.8); 4.021 (1.8); 4.003 (0.6); 3.352 (23.5); 2.892 (0.8); 2.734 (0.7); 2.510 (12.1); 2.505 (16.1); 2.501 (12.1); 2.022 (16.0); 1.990 (7.5); 1.194 (2.0); 1.176 (4.0); 1.158 (2.0); 0.008 (0.4); 0.000 (12.5); −0.008 (0.5)

Example VIII-02: $^1$H-NMR (400.0 MHz, $d_6$-DMSO):

δ = 7.661 (2.3); 7.657 (2.4); 7.641 (2.5); 7.637 (2.5); 7.278 (1.2); 7.274 (1.2); 7.260 (1.7); 7.258 (1.9); 7.256 (2.0); 7.254 (1.6); 7.239 (1.5); 7.235 (1.4); 6.989 (1.4); 6.985 (1.5); 6.969 (2.1); 6.967 (2.1); 6.951 (1.2); 6.947 (1.2); 6.838 (4.8); 6.770 (7.5); 6.579 (2.4); 6.576 (2.5); 6.558 (2.4); 6.555 (2.3); 5.753 (0.6); 5.123 (5.2); 3.323 (14.4); 2.512 (7.2); 2.507 (14.6); 2.503 (19.2); 2.498 (14.0); 2.494 (6.8); 2.029 (16.0); 2.016 (1.0); 0.008 (0.8); 0.000 (21.3); −0.009 (0.8)

Example VIII-03: $^1$H-NMR (400.0 MHz, $d_6$-DMSO):

δ = 9.445 (0.6); 7.517 (2.1); 7.513 (2.2); 7.497 (2.3); 7.493 (2.3); 7.240 (1.0); 7.236 (1.1); 7.219 (2.0); 7.201 (1.4); 7.197 (1.3); 7.055 (1.4); 7.051 (1.4); 7.036 (2.2); 7.032 (2.3); 7.017 (1.2); 7.013 (1.1); 6.987 (0.5); 6.957 (0.6); 6.844 (5.2); 6.826 (0.4); 6.777 (7.1); 6.744 (0.3); 6.738 (0.4); 6.613 (2.4); 6.610 (2.4); 6.592 (2.3); 6.589 (2.2); 5.126 (5.4); 4.055 (0.5); 4.038 (0.5); 3.331 (5.2); 2.509 (7.2); 2.505 (9.3); 2.500 (6.8); 2.141 (1.6); 2.032 (16.0); 1.396 (2.7); 1.347 (0.5); 1.330 (1.0); 1.312 (0.5); 0.008 (0.5); 0.000 (10.3); −0.008 (0.5)

Example VIII-04: $^1$H-NMR (400.0 MHz, $d_6$-DMSO):

δ = 9.545 (0.4); 7.460 (0.4); 7.432 (0.4); 7.351 (1.2); 7.345 (0.9); 7.341 (0.9); 7.336 (0.9); 7.333 (1.0); 7.326 (1.7); 7.322 (1.5); 7.316 (1.2); 7.303 (1.4); 7.298 (1.5); 7.243 (0.7); 7.155 (0.5); 7.144 (0.4); 7.139 (0.7); 7.126 (2.4); 7.120 (3.4); 7.110 (4.6); 7.101 (4.3); 7.096 (1.8); 7.091 (1.8); 7.086 (1.4); 7.072 (0.4); 7.067 (0.3); 6.975 (7.9); 6.922 (0.3); 6.874 (1.3); 6.867 (1.0); 6.865 (1.0); 6.860 (0.9); 6.852 (1.9); 6.848 (2.1); 6.833 (1.2); 6.828 (1.4); 6.822 (0.8); 6.768 (5.6); 5.209 (7.3); 3.327 (10.3); 2.509 (15.5); 2.505 (20.9); 2.500 (16.3); 2.251 (1.0); 2.088 (1.5); 2.062 (16.0); 1.397 (0.6); 0.008 (0.7); 0.000 (17.0)

Example VIII-05: $^1$H-NMR (400.0 MHz, $d_6$-DMSO):

δ = 7.681 (2.8); 7.678 (3.0); 7.661 (3.1); 7.658 (3.1); 7.318 (1.4); 7.314 (1.5); 7.297 (2.7); 7.279 (1.8); 7.275 (1.7); 7.104 (0.4); 7.034 (1.7); 7.031 (1.8); 7.015 (2.9); 7.012 (3.0); 6.996 (1.6); 6.993 (1.8); 6.983 (8.0); 6.944 (0.4); 6.758 (5.6); 6.723 (3.0); 6.720 (3.2); 6.702 (2.9); 6.699 (2.9); 5.244 (7.4); 3.837 (0.3); 3.321 (16.6); 2.525 (0.7); 2.507 (30.6); 2.503 (40.2); 2.498 (30.5); 2.244 (0.9); 2.096 (0.5); 2.069 (16.0); 1.398 (0.5); 0.008 (1.2); 0.000 (28.9)

Example VIII-06: $^1$H-NMR (400.0 MHz, $d_6$-DMSO):

δ = 7.846 (2.2); 7.842 (2.3); 7.826 (2.3); 7.823 (2.3); 7.286 (1.1); 7.283 (1.2); 7.264 (2.0); 7.248 (1.3); 7.244 (1.3); 7.134 (0.5); 7.127 (0.5); 7.115 (0.8); 6.978 (0.7); 6.959 (0.4); 6.916 (0.8); 6.839 (1.3); 6.836 (1.5); 6.816 (6.5); 6.801 (1.3); 6.798 (1.3); 6.766 (8.2); 6.747 (0.7); 6.717 (0.3); 6.711 (0.3); 6.494 (2.3); 6.491 (2.5); 6.473 (2.3); 6.470 (2.3); 5.277 (0.6); 5.113 (3.6); 4.049 (0.6); 4.031 (0.6); 3.321 (8.4); 2.506 (33.3); 2.502 (43.2); 2.497 (32.5); 2.132 (2.0); 2.027 (16.0); 2.015 (3.5); 1.398 (6.3); 1.342 (0.7); 1.324 (1.3); 1.307 (0.6); 0.000 (5.4)

STABILITY DATA EXAMPLES

Stability Towards Hydrolysis in Homogeneous Aqueous Solution—Hydrolysis Stability Test The chemical stability towards hydrolysis of the phenylamidines described in the prior art is good but an improved stability may be an advantage during the preparation and formulation processes in a large scale. The improved stability towards hydrolysis was proven by a hydrolysis stability test as described below:

To produce a suitable preparation of active compound for the hydrolysis stability test, a 1000 ppm stock solution (1 mg/mL) of active compound in acetonitrile is prepared. Three aliquots of 100 μL are pipetted into HPLC vials and diluted with 750 μL acetonitrile. In each vial 850 μL of the appropriate buffer solution (pH4, pH7 and pH9, CertiPUR, Fa. Merck) is added. The buffer containing HPLC vials are incubated in a heated sample tray at 50° C. for 24 hours. The amount A of the active compound is analyzed by HPLC (UV-peak areas at 210 nm) at eight points in time t: 0 min, 140 min, 350 min, 560 min, 770 min, 980 min, 1190 min, 1400 min. The half-life time ($T_{1/2}$) of each active compound is calculated via linear regression by using the following equations (first order degradation assumed):

$$\ln[A(t)] = -kt + \ln[A(0)]$$

$$T^{1/2} = \frac{\ln 2}{k}$$

In table III the results of the hydrolysis stability test are shown for the compounds (I-01), (I-02), (I-03), (I-04) and (I-05) at various pH-values. To demonstrate the improved stability towards hydrolysis in view of phenylamidines known from the art, the results were compared with compound number 1 known from WO2008/110313 and compound no. 337 known from WO2008/110278. The data demonstrate that compounds according to the invention show indeed a higher stability towards hydrolysis. This increased stability will be of advantage during the preparation and formulation processes in a large scale compared to known amidines. The data are to be seen merely by way of example and are not limiting for the purposes of the invention.

TABLE III

| Ex N° | $T_{1/2}$ (pH 7) | $T_{1/2}$ (pH 9) |
|---|---|---|
| I-01 | 67 h | 60 h |
| I-02 | 70 h | 64 h |
| I-03 | 63 h | 53 h |
| I-04 | 83 h | 74 h |
| I-05 | 80 h | 66 h |
| I-06 | 61 h | 55 h |
| Compound no. 1 known from WO2008/110313 | 24 h | 16 h |
| Compound no. 337 known from WO2008/110278 | 25 h | 17 h |

Stability Towards Photolysis—Photolysis Stability Test

The stability towards photolysis of the phenylamidines described in the prior art is good but an improved stability towards photolysis may be an advantage as it could offer a longer lasting efficacy when applied to plants by foliar application. The improved stability towards photolysis was proven by a hydrolysis stability test as described below:

To produce a suitable preparation of active compound for the photolysis stability test, a 1000 ppm stock solution (1 mg/mL) of active compound in acetonitrile is prepared. Aliquots of 25 µL of this stock solution are pipetted in three wells of a Bio-one microtiter plate (MTP) UVStar 96 (Fa. Greiner, Art. No. 655801). The MTP is dried overnight in the dark and then irradiated at 30° C. and 480 W/m² with a UV irradiation device SUNTEST XLS+ or SUNTEST CPS (Fa. Atlas). The amount A of the active compound is analyzed by HPLC (UV-peak areas at 210 nm) at five points in time t: 0 h, 2 h, 4 h, 6 h, 24 h by using the following method: 200 µL acetonitrile is added in the respective well of the MTP and the MTP is sealed with a Bio-one sealing foil, viewseal 80/140 mm (Fa. Greiner, Art. No. 676070). The MTPs are sonicated for 3 minutes and analysed by HPLC. The half-life time ($T_{1/2}$) of each active compound is calculated via linear regression by using the following equations (first order degradation assumed):

$$\ln[A(t)] = -kt + \ln[A(0)]$$

$$T^{1/2} = \frac{\ln 2}{k}$$

In table IV the results of the photolysis stability test are shown for the compounds (I-01) and (I-02). To demonstrate the improved stability towards photolysis in view of phenylamidines known from the art, the results were compared with compound number 1 known from WO2008/110313. The data demonstrate that compounds according to the invention show indeed a higher chemical stability towards photolysis. This increased chemical stability towards photolysis will be of advantage as it will offer a longer lasting efficacy when applied to plants by foliar application compared to known amidines. The data are to be seen merely by way of example and are not limiting for the purposes of the invention.

TABLE IV

| Ex N° | $T_{1/2}$ |
|---|---|
| I-01 | 32 h |
| I-02 | >200 h |
| I-03 | 59 h |
| I-04 | >200 h |
| I-05 | >200 h |
| I-06 | 34 h |
| Compound no. 1 known from WO2008/110313 | 10 h |

Plant Compatibility Test Using Soy Bean Plants

Solvent: 24.5 parts by weight of acetone 24.5 parts by weight of dimethylacetamide Emulsifier: 1 part by weight of alkylaryl polyglycol ether To produce a suitable preparation of active compound, 1 part by weight of active compound is mixed with the stated amounts of solvent and emulsifier, and the concentrate is diluted with water to the desired concentration. Young plants are sprayed with the preparation of active compound at the stated application rate. The plants are then placed in a greenhouse at approximately 21° C. and a relative atmospheric humidity of approximately 80%. The test is evaluated 6 days after application and comprises plant damages like leaf deformation, chlorosis, necrosis, shoot damage or stunting. The results are summarized in table V. 0% means no damages are observed, while 100% means that the plants are totally damaged.

TABLE V

Plant compatibility soy bean

| | Active compound | Rate of application of active compound in ppm | Necrosis in % |
|---|---|---|---|
| | Known from WO2008/110313: | | |
| Ex. 1 | 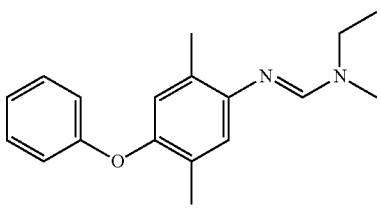 [SMILES: CCN(C)/C=N/c1cc(C)c(Oc2ccccc2)cc1C] | 1000 | 90 |
| | Known from WO2008/110278: | | |
| Ex. 337 | 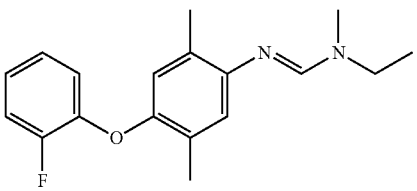 [SMILES: CCN(C)/C=N/c1cc(C)c(Oc2ccccc2F)cc1C] | 1000 | 90 |
| | According to the invention: | | |
| Ex. 1-01 | 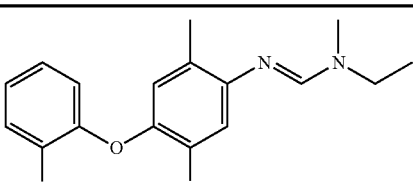 | 1000 | 50 |

USE EXAMPLES

Example: In Vivo Preventive Test on *Phakopsora* Test (Soybeans)

Solvent: 24.5 parts by weight of acetone
24.5 parts by weight of dimethylacetamide
Emulsifier: 1 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for preventive activity, young plants are sprayed with the preparation of active compound at the stated rate of application. After the spray coating has dried on, the plants are inoculated with an aqueous spore suspension of the causal agent of soybean rust (*Phakopsora pachyrhizi*) and stay for 24 h without light in an incubation cabinet at approximately 24° C. and a relative atmospheric humidity of 95%.

The plants remain in the incubation cabinet at approximately 24° C. and a relative atmospheric humidity of approximately 80% and a day/night interval of 12 h.

The test is evaluated 7 days after the inoculation. 0% means an efficacy which corresponds to that of the untreated control, while an efficacy of 100% means that no disease is observed.

In this test, the following compounds according to the invention showed efficacy of at least 70% at a concentration of 10 ppm of active ingredient: I-02

In this test, the following compounds according to the invention showed efficacy of at least 70% at a concentration of 100 ppm of active ingredient: I-01

Example: In Vivo Preventive Test on *Puccinia recondita* (Brown Rust on Wheat)

Solvent: 5% by volume of Dimethyl sulfoxide
10% by volume of Acetone
Emulsifier: 1 µl of Tween® 80 per mg of active ingredient The active ingredients are made soluble and homogenized in a mixture of Dimethyl sulfoxide/Acetone//Tween® 80 and then diluted in water to the desired concentration.

The young plants of wheat are treated by spraying the active ingredient prepared as described above. Control plants are treated only with an aqueous solution of Acetone/Dimethyl sulfoxide/Tween® 80.

After 24 hours, the plants are contaminated by spraying the leaves with an aqueous suspension of *Puccinia recondita* spores. The contaminated wheat plants are incubated for 24 hours at 20° C. and at 100% relative humidity and then for 10 days at 20° C. and at 70-80% relative humidity.

The test is evaluated 11 days after the inoculation. 0% means an efficacy which corresponds to that of the control plants while an efficacy of 100% means that no disease is observed.

In this test, the following compounds according to the invention showed efficacy of at least 70% at a concentration of 500 ppm of active ingredient: I-02

Example: In Vivo Preventive Test on *Pyrenophora teres* (Net Blotch on Barley)

Solvent: 5% by volume of Dimethyl sulfoxide
10% by volume of Acetone

Emulsifier: 1 µl of Tween® 80 per mg of active ingredient

The active ingredients are made soluble and homogenized in a mixture of Dimethyl sulfoxide/Acetone//Tween® 80 and then diluted in water to the desired concentration.

The young plants of barley are treated by spraying the active ingredient prepared as described above. Control plants are treated only with an aqueous solution of Acetone/Dimethyl sulfoxide/Tween® 80.

After 24 hours, the plants are contaminated by spraying the leaves with an aqueous suspension of *Pyrenophora teres* spores. The contaminated barley plants are incubated for 48 hours at 20° C. and at 100% relative humidity and then for 12 days at 20° C. and at 70-80% relative humidity.

The test is evaluated 14 days after the inoculation. 0% means an efficacy which corresponds to that of the control plants while an efficacy of 100% means that no disease is observed.

In this test, the following compounds according to the invention showed efficacy of at least 70% at a concentration of 500 ppm of active ingredient: I-02

Example: In Vivo Preventive Test on *Septoria tritici* (Leaf Spot on Wheat)

Solvent: 5% by volume of Dimethyl sulfoxide
10% by volume of Acetone

Emulsifier: 1 µl of Tween® 80 per mg of active ingredient

The active ingredients are made soluble and homogenized in a mixture of Dimethyl sulfoxide/Acetone//Tween® 80 and then diluted in water to the desired concentration.

The young plants of wheat are treated by spraying the active ingredient prepared as described above. Control plants are treated only with an aqueous solution of Acetone/Dimethyl sulfoxide/Tween® 80.

After 24 hours, the plants are contaminated by spraying the leaves with an aqueous suspension of *Septoria tritici* spores. The contaminated wheat plants are incubated for 72 hours at 18° C. and at 100% relative humidity and then for 21 days at 20° C. and at 90% relative humidity.

The test is evaluated 24 days after the inoculation. 0% means an efficacy which corresponds to that of the control plants while an efficacy of 100% means that no disease is observed.

In this test, the following compounds according to the invention showed efficacy of at least 70% at a concentration of 500 ppm of active ingredient: I-02

The invention claimed is:

1. A phenoxyphenylamidine of formula (I)

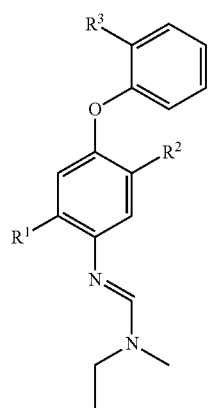

wherein
$R^1$ is methyl;
$R^2$ is selected from the group consisting of halogen and halomethyl;
$R^3$ is halogen;
and/or a salt, N-oxide, metal complex and/or a stereoisomer thereof.

2. The phenoxyphenylamidine according to claim 1 wherein
$R^1$ is methyl;
$R^2$ is selected from the group consisting of fluoro, chloro, bromo, dichloromethyl, trichloromethyl, fluoromethyl, difluoromethyl, and trifluoromethyl;
$R^3$ is selected from the group consisting of bromo, chloro and fluoro.

3. The phenoxyphenylamidine according to claim 1 wherein
$R^1$ is methyl;
$R^2$ is selected from the group consisting of chloro, bromo, difluoromethyl, and trifluoromethyl;
$R^3$ is fluoro, chloro, bromo, and iodo.

4. The phenoxyphenylamidine as claimed in claim 1 selected from the group consisting of N'-[5-chloro-4-(2-fluorophenoxy)-2-methylphenyl]-N-ethyl-N-methylimidoformamide, N'-[4-(2-bromophenoxy)-5-chloro-2-methylphenyl]-N-ethyl-N-methylimidoformamide, N'-[5-chloro-4-(2-chlorophenoxy)-2-methylphenyl]-N-ethyl-N-methylimidoformamide, N-ethyl-N'-[4-(2-fluorophenoxy)-2-methyl-5-(trifluoromethyl)phenyl]-N-methylimidoformamide, N'-[4-(2-bromophenoxy)-2-methyl-5-(trifluoromethyl)phenyl]-N-ethyl-N-methylimidoformamide, and N'-[5-chloro-4-(2-iodophenoxy)-2-methylphenyl]-N-ethyl-N-methylimidoformamide.

5. The phenoxyphenylamidine as claimed in claim 1, wherein the phenoxyphenylamidine is selected from the group consisting of N'-[5-chloro-4-(2-fluorophenoxy)-2-methylphenyl]-N-ethyl-N-methylimidoformamide, N'-[4-(2-bromophenoxy)-5-chloro-2-methylphenyl]-N-ethyl-N-methylimidoformamide, and N-ethyl-N'-[4-(2-fluorophenoxy)-2-methyl-5-(trifluoromethyl)phenyl]-N-methylimidoformamide.

6. A process for preparing a phenoxyphenylamidine as claimed in claim 1 which comprises at least one of the following:
   (a) reaction of nitrobenzene derivative of formula (III) with phenol derivative of formula (II) according to the reaction scheme below:

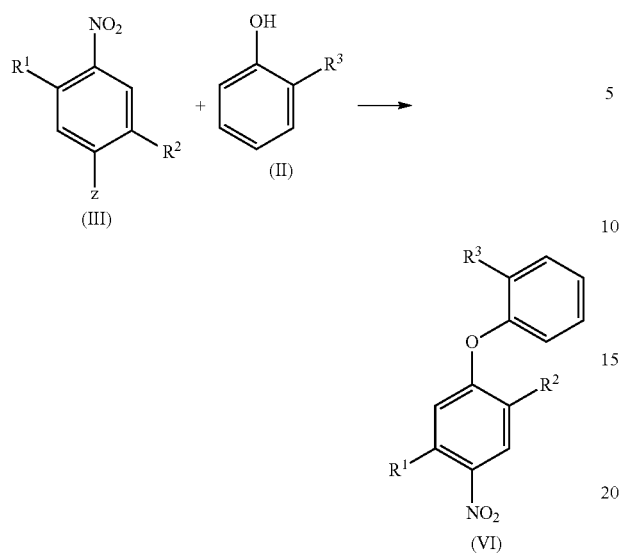

(b) reaction of a nitrophenol derivative of formula (V) with a phenyl derivative of formula (IV) according to the reaction scheme below:

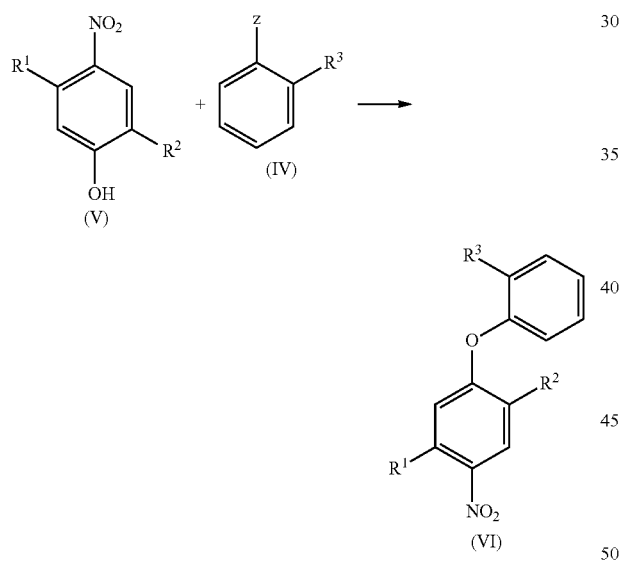

(c) reaction of an aniline of formula (VII) with a phenol derivative of formula (II) according to the reaction scheme below:

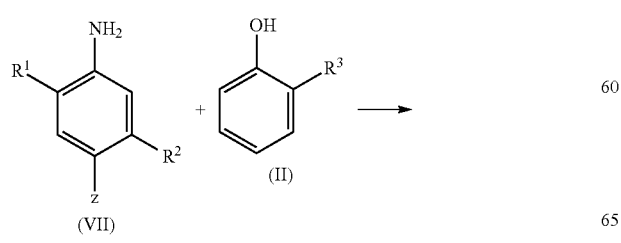

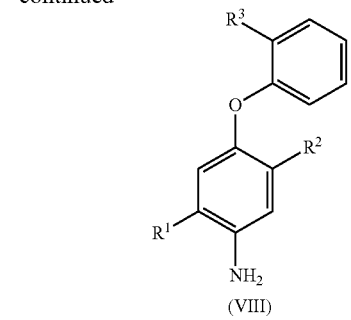

(d) reaction of an aminophenol of formula (XII) with a phenyl derivative of formula (IV) according to the reaction scheme below:

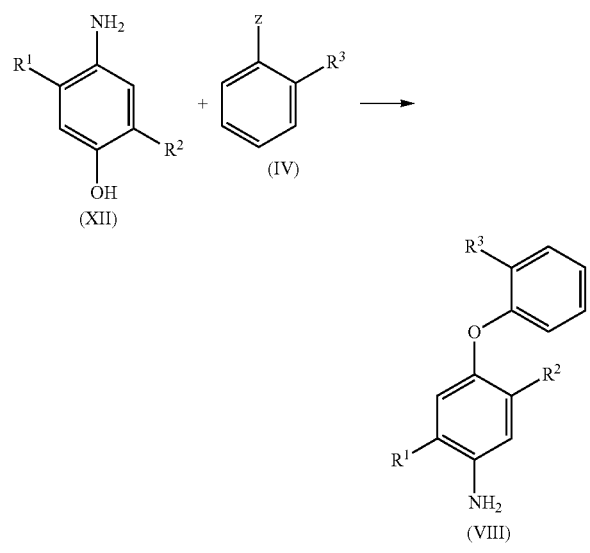

(e) reduction of a nitrophenyl ether of formula (VI) to an aminophenyl ether of formula (VIII) according to the reaction scheme below:

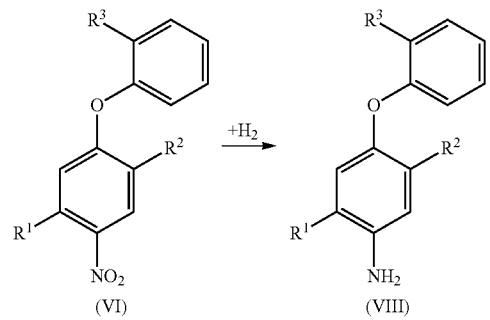

(f) reaction of an aminophenyl ether of formula (VIII) with
  (i) aminoacetal of formula (XIII) or
  (ii) with N-ethyl-N-methylformamide of formula (XIV) or
  (iii) with N-methylethanamine of formula (XV) in the presence of ortho ester of formula (XVI)

according to the reaction scheme below:

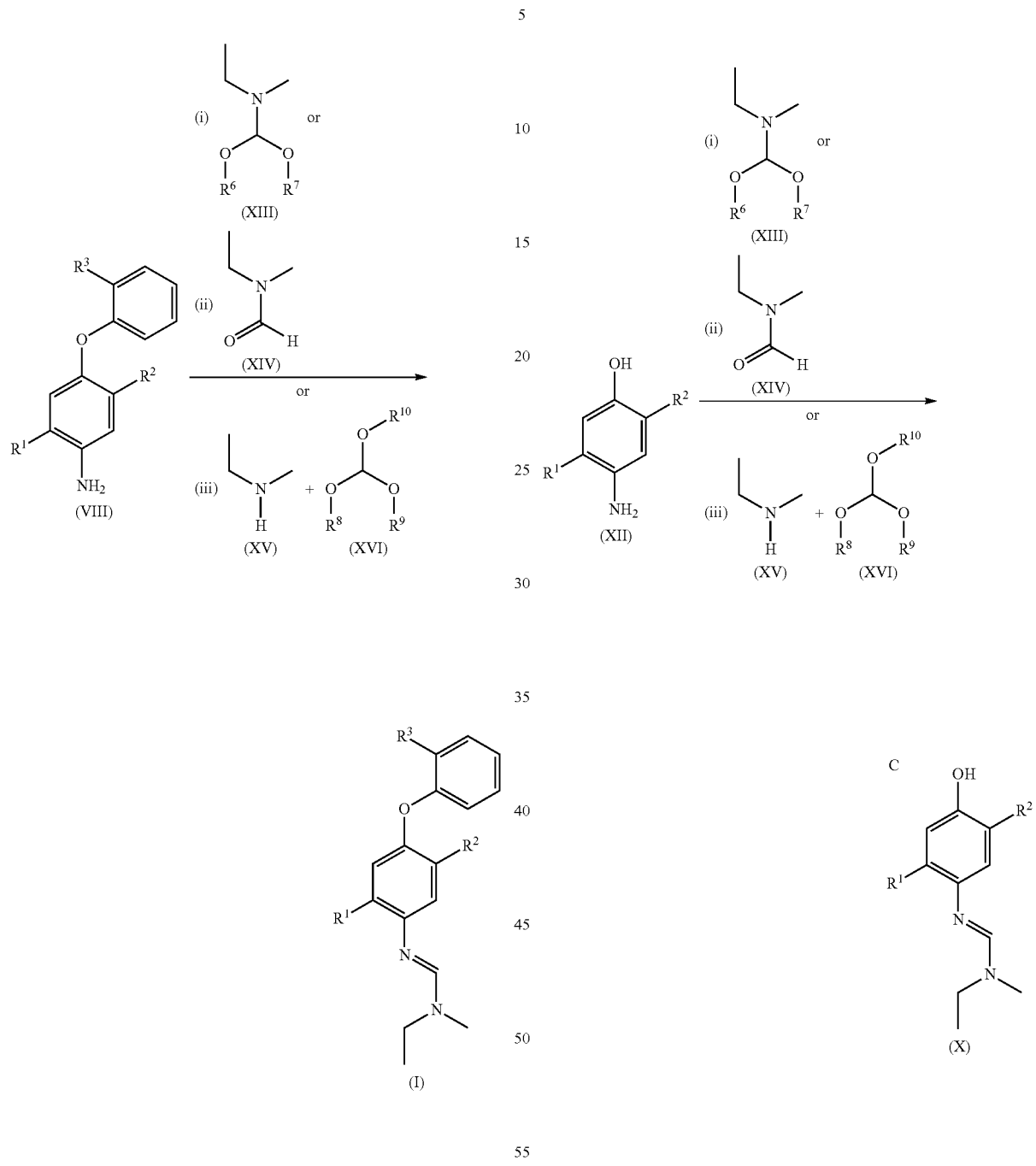

(g) reaction of aminophenol of formula (XII) with
  (i) aminoacetal of formula (XIII) or
  (ii) with N-ethyl-N-methylformamide of formula (XIV) or
  (iii) with N-methylethanamine of formula (XV) in the presence of ortho ester of formula (XVI)

(h) reaction of aniline of formula (VII) with
  (i) aminoacetal of formula (XIII) or
  (ii) with N-ethyl-N-methylformamide of formula (XIV) or
  (iii) with N-methylethanamine of formula (XV) in the presence of ortho ester of formula (XVI) according to the reaction scheme below:

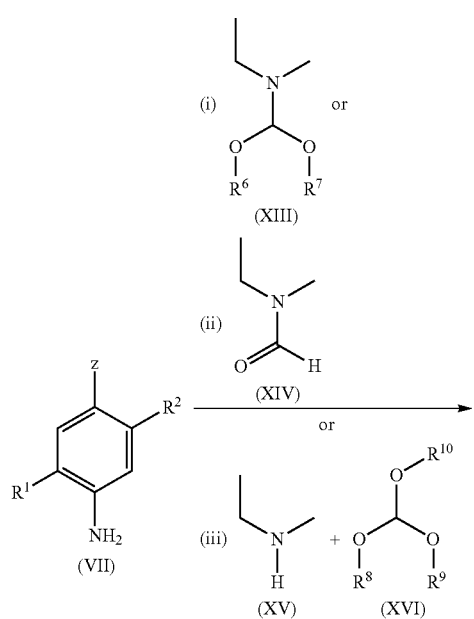

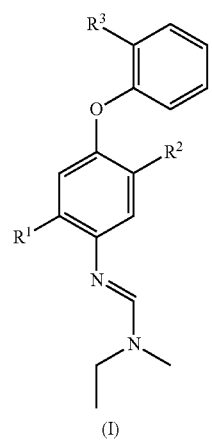

(j) reaction of amidine of formula (XI) with a phenyl derivative of formula (IV) according to the reaction scheme below:

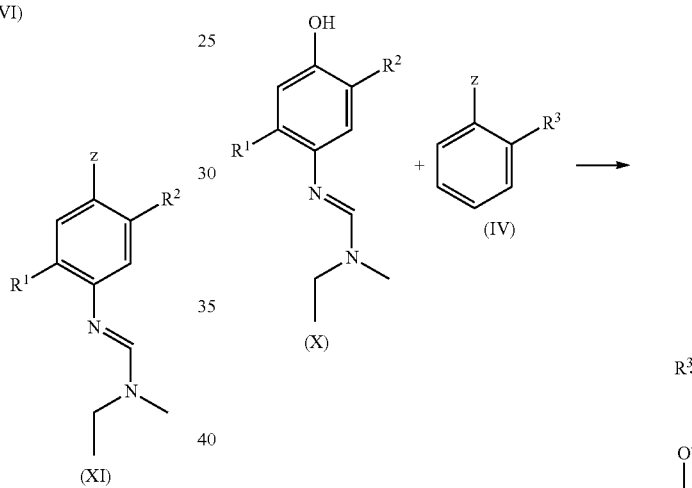

(i) reaction of amidine of formula (XI) with a phenol derivative of formula (II) according to the reaction scheme below:

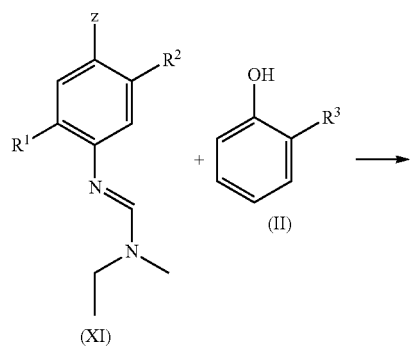

wherein in the above schemes
Z is a leaving group;
$R^6$ and $R^7$ independently of one another are selected from the group consisting of $C_{1-12}$-alkyl, $C_{2-12}$-alkenyl, $C_{2-12}$-alkynyl, $C_{5-18}$-aryl, and $C_{7-19}$-arylalkyl groups and together with the atoms to which they are attached may form a five-, six- or seven-membered ring;
$R^8$ to $R^{10}$ independently of one another are selected from the group consisting of $C_{1-12}$-alkyl, $C_{2-12}$-alkenyl, $C_{2-12}$-alkynyl, $C_{5-18}$-aryl, $C_{7-19}$-arylalkyl, and $C_{7-19}$-alkylaryl groups and in each case $R^8$ with $R^9$, $R^9$ with $R^{10}$ or $R^8$ with $R^{10}$ together with the atoms to which they are attached and optionally together with further carbon, nitrogen, oxygen or sulfur atoms may form a five-, six- or seven-membered ring.

7. A nitrophenyl ether of formula (VI)

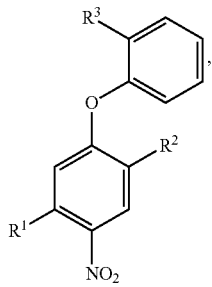

(VI)

wherein

R¹ is methyl; and

R² is selected from the group consisting of bromo and halomethyl and R³ is halogen, or R² is chloro and R³ is selected from the group consisting of fluoro, bromo, and iodo.

8. The nitrophenyl ether of formula (VI) according to claim 7, wherein

R² is selected from the group consisting of bromo, difluoromethyl, and trifluoromethyl, and R³ is halogen, or R² is chloro and R³ is selected from the group consisting of fluoro, bromo, and iodo.

9. The nitrophenyl ether of formula (VI) according to claim 7, wherein

R² is chloro; and

R³ is fluoro or bromo.

10. The nitrophenyl ether of formula (VI) according to claim 7, wherein

R² is trifluoromethyl; and

R³ is fluoro.

11. An aminophenyl ether of formula (VIII)

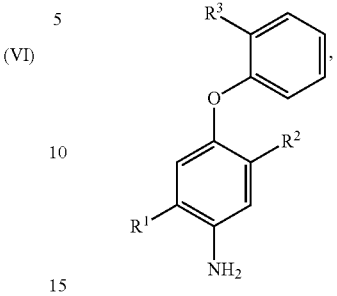

(VIII)

wherein

R¹ is methyl; and

R² is chloro and R³ is selected from the group consisting of fluoro, bromo, and iodo, or R² is halomethyl and R³ is halogen.

12. The aminophenyl ether of formula (VIII) according to claim 11, wherein

R² is chloro; and

R³ is fluoro or bromo.

13. The aminophenyl ether of formula (VIII) according to claim 11, wherein

R² is trifluoromethyl; and

R³ is fluoro.

14. An agrochemical formulation for controlling unwanted microorganisms, comprising at least one phenoxyphenylamidine as claimed in claim 1.

15. A seed treated with at least one phenoxyphenylamidine as claimed in claim 1.

16. A method for controlling unwanted microorganisms, comprising applying a substituted phenoxyphenylamidine as claimed in claim 1 or agrochemical formulation thereof to the microorganisms and/or a habitat thereof.

17. The method according to claim 16, wherein seed is treated.

18. The method according to claim 16, wherein a transgenic plant is treated.

19. The method according to claim 16, wherein a transgenic seed is treated.

20. A method for protecting seed against unwanted microorganisms comprising treating seed with at least one phenoxyphenylamidine as claimed in claim 1.

* * * * *